US008818498B2

(12) United States Patent
Terada et al.

(10) Patent No.: US 8,818,498 B2
(45) Date of Patent: Aug. 26, 2014

(54) ELECTROENCEPHALOGRAM INTERFACE SYSTEM

(75) Inventors: Yoshihisa Terada, Tokyo (JP); Koji Morikawa, Kyoto (JP)

(73) Assignee: Panasonic Corporation, Osaka (JP)

( * ) Notice: Subject to any disclaimer, the term of this patent is extended or adjusted under 35 U.S.C. 154(b) by 713 days.

(21) Appl. No.: 12/955,016

(22) Filed: Nov. 29, 2010

(65) Prior Publication Data

US 2011/0071416 A1    Mar. 24, 2011

Related U.S. Application Data

(63) Continuation of application No. PCT/JP2010/000197, filed on Jan. 15, 2010.

(30) Foreign Application Priority Data

Jan. 19, 2009  (JP) .................................. 2009-009179

(51) Int. Cl.
*A61B 5/04* (2006.01)

(52) U.S. Cl.
USPC ............................ 600/544; 600/383; 600/545

(58) Field of Classification Search
USPC ......................................... 600/383, 544, 545
See application file for complete search history.

(56) References Cited

U.S. PATENT DOCUMENTS

| 4,579,125 | A * | 4/1986 | Strobl et al. ................... 600/544 |
| 2003/0195588 | A1 * | 10/2003 | Fischell et al. .................. 607/55 |
| 2004/0034645 | A1 | 2/2004 | Manabe et al. |
| 2005/0085741 | A1 * | 4/2005 | Hoskonen et al. ............. 600/544 |
| 2007/0179396 | A1 * | 8/2007 | Le et al. ........................ 600/544 |
| 2008/0306398 | A1 | 12/2008 | Uchiyama et al. |
| 2009/0187114 | A1 * | 7/2009 | Morikawa et al. ............ 600/545 |
| 2009/0253996 | A1 * | 10/2009 | Lee et al. ....................... 600/544 |
| 2010/0317988 | A1 * | 12/2010 | Terada et al. ................. 600/544 |

FOREIGN PATENT DOCUMENTS

| JP | 59-174804 | 11/1984 |
| JP | 02-026534 | 1/1990 |
| JP | 6-70704 | 10/1994 |
| JP | 2000-041962 | 2/2000 |

(Continued)

OTHER PUBLICATIONS

International Search Report for corresponding International Application No. PCT/JP2010/000197 mailed Mar. 2, 2010.

(Continued)

*Primary Examiner* — Michael Kahelin
*Assistant Examiner* — Mitchell Alter
(74) *Attorney, Agent, or Firm* — Renner, Otto, Boisselle & Sklar, LLP

(57) ABSTRACT

An eyeglass-type electroencephalogram interface system is worn on the head of a user. The system includes: an output section for presenting a visual stimulation to the user; an ear electrode portion disposed at a position coming in contact with an ear of the user when the system is worn; a facial electrode portion disposed at a position coming in contact with the face below a straight line connecting an external canthus and an internal canthus of an eye of the user, such that the mass of the system is supported at the position, when the system is worn; and an electroencephalogram measurement and determination section for measuring an event-related potential on the basis of a potential difference between the ear electrode portion and the facial electrode portion based on the visual stimulation being presented by the output section as a starting point.

9 Claims, 22 Drawing Sheets

(56) References Cited

FOREIGN PATENT DOCUMENTS

| | | |
|---|---|---|
| JP | 2001-100144 | 4/2001 |
| JP | 2001-187034 | 7/2001 |
| JP | 2001-340312 | 12/2001 |
| JP | 2003-157136 | 5/2003 |
| JP | 2004-016658 | 1/2004 |
| JP | 2004-350797 | 12/2004 |
| JP | 2005-034620 | 2/2005 |
| JP | 2006-196995 | 7/2006 |
| JP | 2006-212348 | 8/2006 |
| JP | 2006-295520 | 10/2006 |
| JP | 2006-340986 | 12/2006 |
| JP | 2008-099834 | 5/2008 |
| WO | 2008/152799 A1 | 12/2008 |

OTHER PUBLICATIONS

Form PCT/ISA/237 for corresponding International Application No. PCT/JP2010/000197 dated Mar. 2, 2010 and partial English translation.

Morikawa et al., "Developing Usability Testing Method Based on Event-Related Brain Potential", Matsushita Technical Journal, vol. 53, No. 1, p. 51, Oct. 2007.

* cited by examiner

FIG.2

| | | MEASUREMENT ELECTRODE | | | | | | |
|---|---|---|---|---|---|---|---|---|
| | | AVERAGE | ABOVE LEFT EAR | ALONGSIDE LEFT EYE | ABOVE LEFT EYE | NOSE | ABOVE RIGHT EYE | ALONGSIDE RIGHT EYE | ABOVE RIGHT EAR |
| REFERENCE ELECTRODE | ABOVE LEFT EAR | 47.7% | – | 48.4% | 56.6% | 43.8% | 53.4% | 36.9% | 46.9% |
| | ALONGSIDE LEFT EYE | 47.0% | 48.4% | – | 57.2% | 40.9% | 45.6% | 37.8% | 51.9% |
| | ABOVE LEFT EYE | 54.1% | 56.6% | 57.2% | – | 63.8% | 31.6% | 54.4% | 61.3% |
| | NOSE | 50.6% | 43.8% | 40.9% | 63.8% | – | 55.6% | 40.6% | 58.8% |
| | ABOVE RIGHT EYE | 52.7% | 53.4% | 45.6% | 31.6% | 55.6% | – | 65.9% | 63.8% |
| | ALONGSIDE RIGHT EYE | 47.9% | 36.9% | 37.8% | 54.4% | 40.6% | 65.9% | – | 51.6% |
| | ABOVE RIGHT EAR | 55.7% | 46.9% | 51.9% | 61.3% | 58.8% | 63.8% | 51.6% | – |

FIG.3

| | | MEASUREMENT ELECTRODE | | | | | | |
|---|---|---|---|---|---|---|---|---|
| | | AVERAGE | ABOVE LEFT EAR | ALONGSIDE LEFT EYE | ABOVE LEFT EYE | NOSE | ABOVE RIGHT EYE | ALONGSIDE RIGHT EYE | ABOVE RIGHT EAR |
| REFERENCE ELECTRODE | LEFT MASTOID | 57.8% | 50.0% | 62.5% | 67.5% | 59.1% | 62.8% | 48.4% | 54.4% |
| | RIGHT MASTOID | 66.6% | 52.2% | 68.8% | 75.0% | 64.7% | 75.3% | 62.2% | 68.1% |

ELECTROENCEPHALOGRAM INTERFACE SYSTEM

This is a continuation of International Application No. PCT/JP2010/000197, with an international filing date of Jan. 15, 2010, which claims priority of Japanese Patent Application No. 2009-009179, filed on Jan. 19, 2009, the contents of which are hereby incorporated by reference.

BACKGROUND OF THE INVENTION

1. Field of the Invention

The present invention relates to an interface (electroencephalogram interface) system for allowing a device to be manipulated by utilizing an electroencephalogram.

2. Description of the Related Art

In recent years, wearable devices such as head-mount displays (hereinafter also referred to as "HMDs") are gaining prevalence due to decreases in the size and weight of devices. Normally, as interfaces of devices, methods such as pressing a button, moving a cursor to make a decision, and manipulating a mouse while looking at a screen have been used. However, if the aforementioned physical device manipulations are required when manipulating a device whose body has a small size and which is characterized to be handsfree, e.g., an eyeglass-type HMD, the handsfree feature will be undermined, thus being ineffective. Therefore, attention is drawn to interfaces for easily controlling a device without performing any physical manipulations, specifically, interfaces utilizing an electroencephalogram that make it possible to quickly control a device by merely thinking.

An electroencephalogram is an encephalic activity (electrical activity of cranial nerve cells) measured as an electrical signal based on a difference in potential between a reference electrode and an measurement electrode. An example of an interface utilizing an electroencephalogram is a method and apparatus of determining a human psychological state and the like by utilizing an event-related potential which is described in Japanese Laid-Open Patent Publication No. 2005-34620 which is referred to as "Patent Document 1". Patent Document 1 discloses a technique of determining an option which a user wishes to select by utilizing a characteristic signal of an event-related potential of his or her electroencephalogram.

Specifically, an electroencephalogram interface has been realized in which an electrode is worn on the parietal; words are randomly displayed on a screen; and a word which is selected by a user is determined by utilizing a positive component (P300 component) that appears in a time slot from 300 ms to 500 ms based on the timing of displaying the word which the user wishes to select as a starting point, for example.

In a conventional electroencephalogram measurement, electrodes are worn according to the position notation of the International 10-20 system, such that measurement is performed with a measurement electrode being worn on the head. In Patent Document 1, an electroencephalogram measurement is performed by using a characteristic signal at a Pz (median parietal) position or a Cz (median center) position according to the International 10-20 system. It is known that the characteristic signal utilized in Patent Document 1 is intensely measured at the location of the Pz position. Therefore, Pz is mainly used as an electrode position of conventional electroencephalogram interfaces.

However, generally speaking, an electroencephalogram measurement must be performed by using an electrode which is worn at the parietal as mentioned above. Therefore, in the case where a device which does not have a structure to come in contact with the parietal (e.g., the aforementioned HMD) is used, it is necessary for the electroencephalograph to have a shape extending across the head, as in a pair of overhead-type headphones. However, since there is a strong need for downsizing any wearable device to be worn on the face such as an HMD, it is highly likely that the portion extending across the head (as in headphones) will be considered unnecessary in the future. Moreover, a shape extending across the head is aesthetically poor, and may make the hair messy when worn, and thus is not an idealistic HMD shape of the future. Thus, it is a prerequisite for an HMD shape not to extend across the head.

In view of the above circumstances, in order to use an HMD-type device in combination with an electroencephalogram interface, it is necessary to separately wear an electrode for measuring an electroencephalogram at the parietal by some means, other than the HMD itself.

For example, Japanese Laid-Open Patent Publication No. 2004-16658, which is referred to as "Patent Document 2", discloses a method in which each a plurality of corded electrodes included in an HMD is attached at a desired place (head) (FIG. 4).

However, an HMD is a device which is frequently put on or taken off, rather than being perpetually worn. Therefore, it will be a great burden on the user to have to separately wear a device in addition to the HMD.

In answer thereto, an example of performing an electroencephalogram measurement by placing electrodes within the range of an eyeglasses shape is disclosed in Japanese Laid-Open Utility Model Publication No. 6-70704 which is referred to as "Patent Document 3". FIG. 24 shows the construction of a device for electroencephalogram electrode attachment which is disclosed in Patent Document 3. This device for electroencephalogram electrode attachment includes an elastic contact belt inside a C-shaped headband, such that electrodes which are placed on the contact belt enable electroencephalogram measurements. In accordance with this device for electroencephalogram electrode attachment, the electrodes are simultaneously worn when the device is worn, which eliminates the need to separately wear another device, so that the user's burden of device wearing is reduced.

However, when constructing an eyeglass-type electroencephalogram interface apparatus by using the construction of Patent Document 3, it is necessary to dispose an output section for presenting a visual stimulation at the position of a lens of the eyeglasses, so that the electrodes disposed on the face front are likely to be shifted. The reason is that the construction of Patent Document 3 supports the wearable device via support at the user's temples, which is achieved through clamping of the headband, and via support at the user's forehead, which is achieved through pressuring of the contact belt.

Any wearable device is supported by being pressed against a user. Therefore, if a video output device or the like is disposed at the position of a lens of the eyeglasses, an increased weight will act on the wearable device front, thus making it likely for the electrodes disposed on the contact belt (i.e., disposed at the face front) to be shifted in a downward direction.

In order to reduce shifting of the electrodes, the clamping of the headband or the pressuring of the contact belt may be increased in intensity. However, an increased pressuring on the user will lead to an increased burden on the user associated with clamping, which makes long hours of wearing difficult.

SUMMARY OF THE INVENTION

The present invention has been made in view of the above problems, and an objective thereof is to provide an electroencephalogram interface system which ensures stable electrode contact, without increasing a user's burden through increased clamping against the user.

An electroencephalogram interface system according to the present invention is an eyeglass-type electroencephalogram interface system to be worn on a head of a user, comprising: an output section for presenting a visual stimulation to the user; an ear electrode portion disposed at a position coming in contact with an ear of the user when the eyeglass-type electroencephalogram interface system is worn; a facial electrode portion disposed at a position coming in contact with a face of the user below a straight line connecting an external canthus and an internal canthus of an eye of the user, such that the mass of the eyeglass-type electroencephalogram interface system is supported at the position, when the eyeglass-type electroencephalogram interface system is worn; and an electroencephalogram measurement and determination section for measuring an event-related potential on the basis of a potential difference between the ear electrode portion and the facial electrode portion, based on a timing of presenting the visual stimulation as a starting point.

The facial electrode portion may be a nose pad portion of the eyeglass-type electroencephalogram interface system.

The ear electrode portion may be disposed on a same side as the facial electrode portion with respect to the straight line connecting the external canthus and the internal canthus of an eye of the user.

The ear electrode portion may come in contact with the user behind an ear.

The electroencephalogram measurement and determination section may hold a determination criterion database storing data of a plurality of waveforms concerning event-related potentials; the determination criterion database may store data of a waveform of an event-related potential appearing when wishing to make a selection and data of a waveform of an event-related potential appearing when not wishing to make a selection; and the electroencephalogram measurement and determination section may cause a process associated with the visual stimulation to be executed when determining that a waveform of the measured event-related potential is closest to that of the event-related potential when wishing to make a selection.

The electroencephalogram interface system may further comprise a facial electrode position determination section for determining a position of the facial electrode portion based on whether, in the electroencephalogram signal of the user, an amplitude of a signal associated with a blink of the user falls between a predetermined upper threshold value and a predetermined lower threshold value.

The electroencephalogram measurement and determination section may measure the electroencephalogram signal based on a potential difference between the ear electrode portion and the facial electrode portion; and in the measured electroencephalogram signal, the facial electrode position determination section may regard a signal in a predetermined frequency band as a signal associated with a blink of the user.

In the measured electroencephalogram signal, the facial electrode position determination section may regard a signal in a frequency band of 1.7 Hz to 2.2 Hz as a signal associated with a blink of the user.

When an amplitude of a signal associated with a blink of the user is greater than the upper threshold value or smaller than the lower threshold value, the output section may present an alarm indicating that the eyeglass-type electroencephalogram interface system is shifted in position.

According to the present invention, a user is not substantially burdened with the need to wear a separate device for electrode attachment or an increased clamping by a device fixture, etc., and an electroencephalogram interface system can be realized with electrodes which are contained within the range of an eyeglasses shape.

Other features, elements, processes, steps, characteristics and advantages of the present invention will become more apparent from the following detailed description of preferred embodiments of the present invention with reference to the attached drawings.

BRIEF DESCRIPTION OF THE DRAWINGS

FIG. 2 is a table showing accuracy results in the case of using an electrode disposed on the face as a reference electrode.

FIG. 3 is a table showing accuracy results taken on the basis of right and left ear mastoids (the left mastoid and the right mastoid).

DETAILED DESCRIPTION OF PREFERRED EMBODIMENTS

Hereinafter, with reference to the attached drawings, embodiments of the electroencephalogram interface system according to the present invention will be described.

In order to realize an electroencephalogram interface system with electrodes which are within the range of an eyeglasses shape, it is necessary to identify places where electrodes can be stably disposed, or electrode positions where not much noise will be mixed.

First, the inventors conducted a search as to which positions, within the range of the shape of an eyeglass-type wearable device, are the most effective electrode positions. Herein, an "eyeglass-type head-mount display" is taken as an example. An "eyeglass-type head-mount display" will hereinafter be simply referred to as an "HMD". In the descriptions of the following embodiments, it is assumed that each HMD shape does not extend across the head of the user.

In the present specification, it is assumed that "the range of the shape" of a wearable device such as an HMD refers to a range which is occupied by a shape which is normally required of that device. In order to find an electrode positioning which makes it possible to provide an electroencephalogram interface having a similar accuracy to that obtained by disposing an electrode on the head, it is necessary to know electrode positions which will achieve a high distinction ratio within the range of an HMD shape first. Prior to descriptions of the embodiments, an experiment which was performed by the inventors to search for optimum reference electrode positions within the range of an HMD shape will be described.

Figure 5:
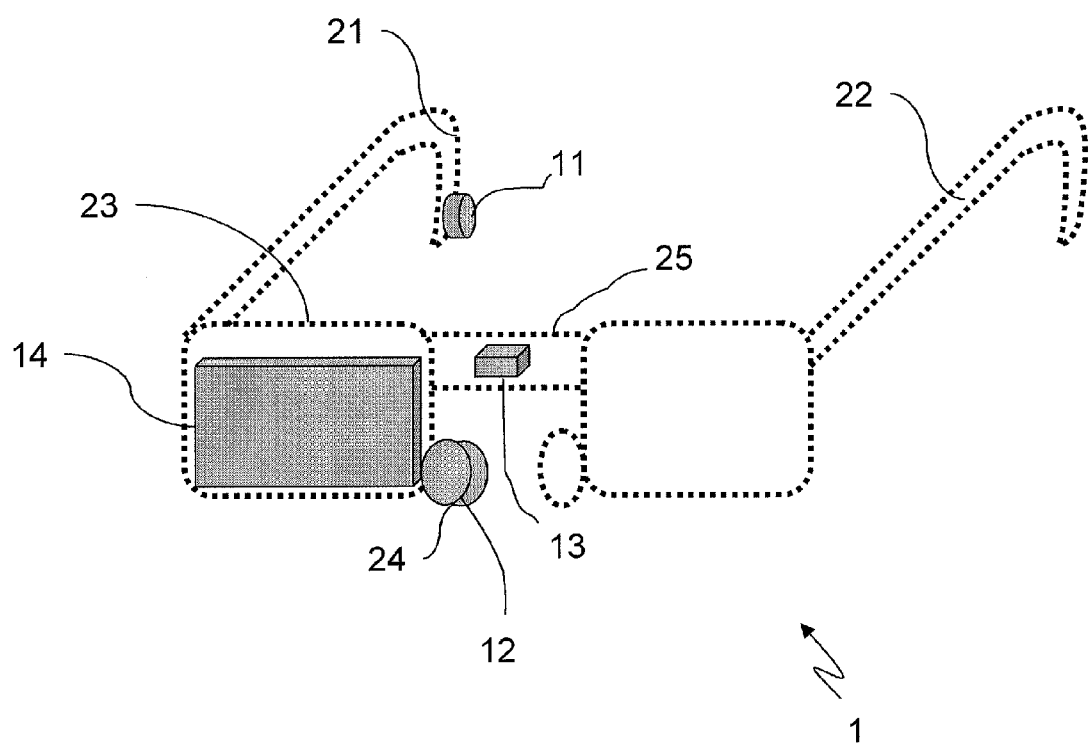
FIG. 5 is a diagram showing an exemplary device shape of the electroencephalogram interface system 1.

FIG. 1 shows electrode positions that are contained within the range of an HMD shape. The HMD shape is as shown in FIG. 5, for example. FIG. 5 will be described in detail later.

Figure 1A:
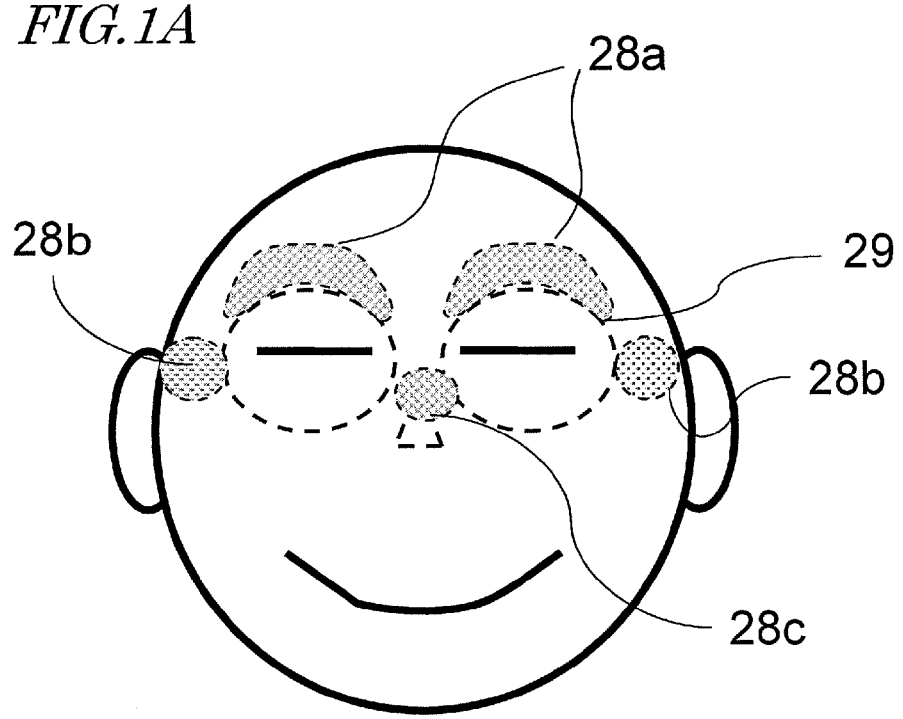
FIGS. 1A and 1B are diagrams showing electrode positions that are contained within the range of an HMD shape.

As shown in FIG. 1A, electrodes "above the eyes" 28a are worn at the upper edges of eye sockets 29; electrodes "alongside the eyes" 28b are worn at the outer edges of the eye sockets 29 (outer corners of the eye lids); a nose electrode is worn at the nasion 28; and electrodes "above the ear" are worn at ear-root superior portions 30e. In view of the range of an HMD shape, not only the facial electrodes which are employed in electro-oculographic potential measurement, but portions in the ear periphery, e.g., earlobes 30b, opisthotics 30d (behind the ear roots), infraotics (under the ear roots), and prootics 30c (shown in FIG. 1B; the ranges delineated by broken lines at the mastoid 30a, earlobe 30b, tragus 30c, and ear root posterior 30d) can also be utilized as targets of measurement in an HMD shape. Therefore, the inventors have chosen the mastoid 30a, which is a protrusion of the cranium at the hind roots of the ears, as a representative of the aforementioned ear periphery.

For the experiment, positions shown in FIG. 1 were used as exemplary positions within an HMD shape that are in contact with the face of a user, and a specific study of accuracy was performed by utilizing these portions.

In the experiment, a measurement experiment was performed for 15 test subjects in their twenties, among whom test subjects that maintained a high arousal level were subjected to analysis.

As for the electroencephalogram measurement, Polymate AP-1124 (manufactured by DIGITEX LAB. CO., LTD) was used, with a sampling frequency of 200 Hz and a time constant of 3 seconds, and with a 30 Hz low-pass filter being used for filtering.

In this experiment, by using each electrode shown in FIG. 1 as a reference electrode, an electroencephalogram was measured based on a potential difference from another electrode, thus conducting an electroencephalogram interface evaluation experiment. Each test subject was asked to make 40 selections, and the rate at which correct results of determination were obtained was calculated as the distinction ratio, thus performing an accuracy check.

With a similar technique, an electroencephalogram measurement was performed with a measurement electrode at the parietal (Pz), thus resulting in a distinction ratio of 81.3%.

In order to search for optimum reference electrode positions on the face, electroencephalograms were measured with combinations of electrodes at positions shown in FIG. 1, and comparisons were made with respect to the distinction ratio of the electroencephalogram interface. The relationship between the electrode combinations and the distinction ratio is shown in FIG. 2 and FIG. 3.

FIG. 2 shows accuracy results in the case of using an electrode disposed on the face as a reference electrode, whereas FIG. 3 shows accuracy results taken on the basis of right and left ear mastoids (the left mastoid and the right mastoid). The experimental results of FIG. 3 indicate an average distinction ratio of 57.8% on the basis of the left mastoid, and 66.6% on the basis of the right mastoid. This indicates that an electroencephalogram obtained by measuring a facial potential on the basis of the right or left mastoid provides a higher average distinction ratio than that of an electroencephalogram measured on the basis of any facial electrode shown in FIG. 2, and contains an electroencephalogram signal that is necessary for allowing the below-described electroencephalogram interface system to operate. When a distinction ratio was measured for the electrode above the left eye with the reference electrode at the right mastoid, a distinction ratio of 75.0% was obtained, and similarly, the electrode above the right eye provided a distinction ratio of 75.3%, both resulting in an accuracy of a little less than 80%, which is the almost same distinction ratio as that of the case where a measurement is taken at the parietal. This is presumably because disposing a reference electrode at a mastoid allows a portion of the brain to be included between the mastoid and the facial electrode, thus making it possible to measure part of the encephalic activity by measuring a potential difference therebetween, which resulted in the high distinction ratios.

Thus it was confirmed that, by measuring an electroencephalogram from a potential difference of a facial electrode on the basis of the ear periphery (particularly a mastoid), electroencephalogram measurements can be made with a similar accuracy to that of the case where an electroencephalogram is measured at the parietal, such that a sufficient performance can be obtained without wearing an electrode at the parietal.

Therefore, in order to construct an electroencephalogram interface system with a good accuracy, it is necessary to dispose at least one electrode which works on the basis of the ear periphery (mastoid).

Next, the inventors have studied positions where not much noise will be mixed, within the range of the shape of an eyeglass-type wearable device.

One noise factor in electroencephalogram measurements is the noises due to blinking. When an electrode is disposed within the range of the shape of an eyeglass-type wearable device (i.e., the face), blinks will be measured as large noises because of the short distance between the electrode and the eyeballs. Therefore, it is important to dispose an electrode at a position where blink noise is unlikely to be mixed.

First, the mechanism by which blink noise may be mixed will be described. At blinking, an eyelid slides over the cornea. The cornea of the eyeball is positively charged, and as the eyelid rubs against the cornea, the positive potential of the cornea is transmitted to the eyelid. The positive potential having been transmitted to the eyelid is then transmitted to the electrode which is disposed above the eye, thus being measured as a blink noise.

Figure 22:
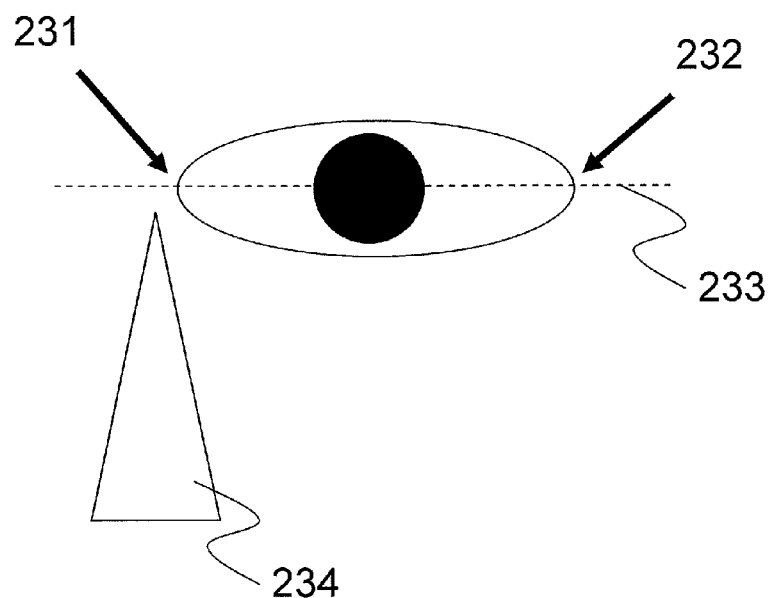
FIG. 22 is a diagram showing relative positioning of an internal canthus 231 and an external canthus 232.

FIG. 22 shows relative positioning of an internal canthus 231 and an external canthus 232 around an eye. The example shown in FIG. 22 illustrates the left eye. Before and after a blink, the eyelid is positioned above a straight line 233 connecting the internal canthus 231 and the external canthus 232, and therefore propagation of the positive potential is also considered to occur above the straight line 233. Therefore, by disposing a facial electrode below the straight line 233 connecting the internal canthus 231 and the external canthus 232, an electroencephalogram measurement becomes possible presumably with reduced influence of blink noise. To give an example, a facial electrode may be provided at the nasion of the nose 234, which is located below the straight line 233 in FIG. 22. In the case of an eyeglass-type electroencephalogram interface system such as an HMD, such a facial electrode will function as a nose pad. Furthermore, by disposing the aforementioned ear-periphery electrode at the same side as the facial electrode with respect to the straight line 233, e.g., at the mastoid 30a or the opisthotic 30d, the influence of blink noise can be suppressed with greater certainty.

Embodiment 1

Figure 4:
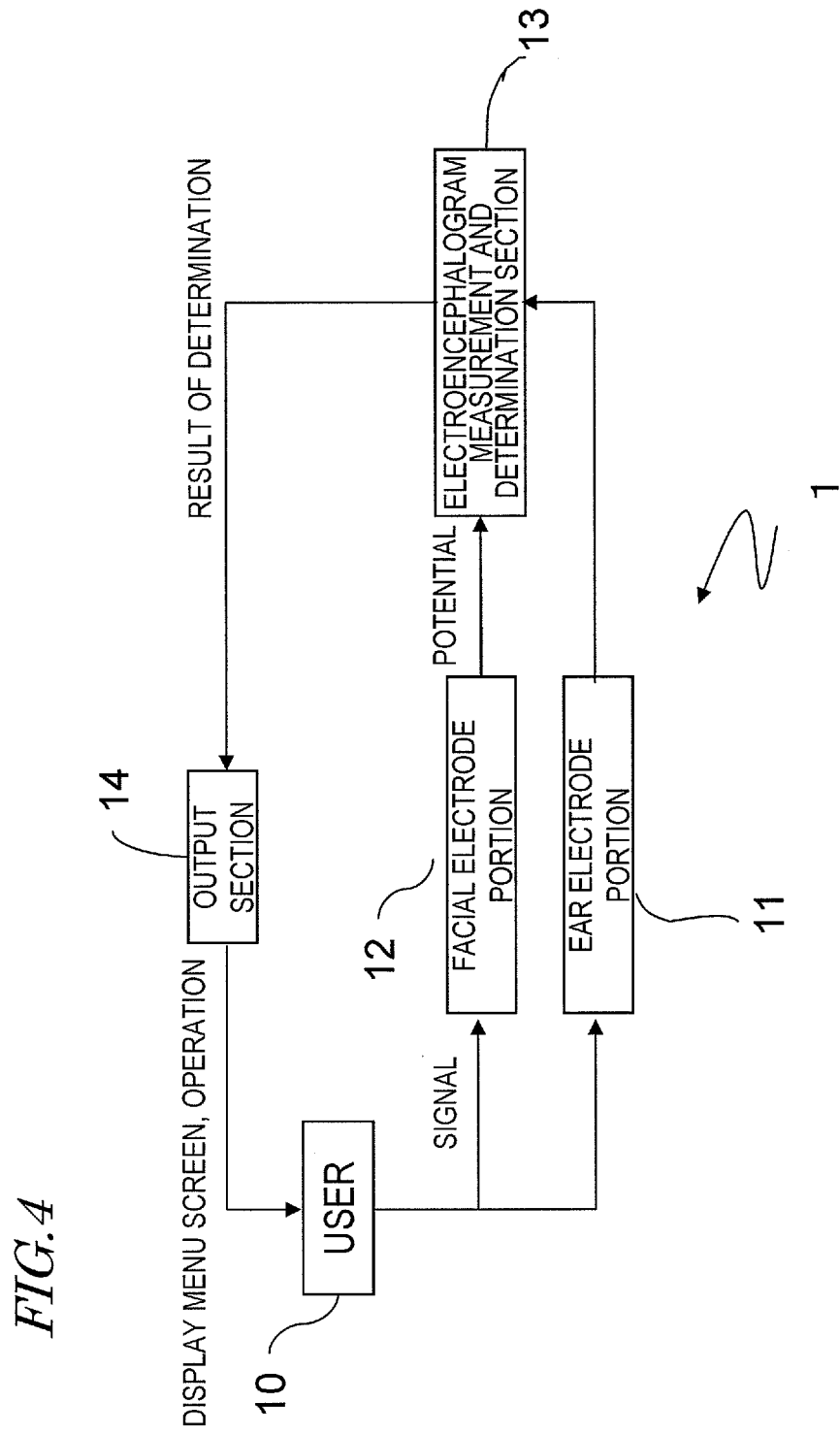
FIG. 4 is a diagram showing a functional block construction of an electroencephalogram interface system 1 of an embodiment.
Figure 6:
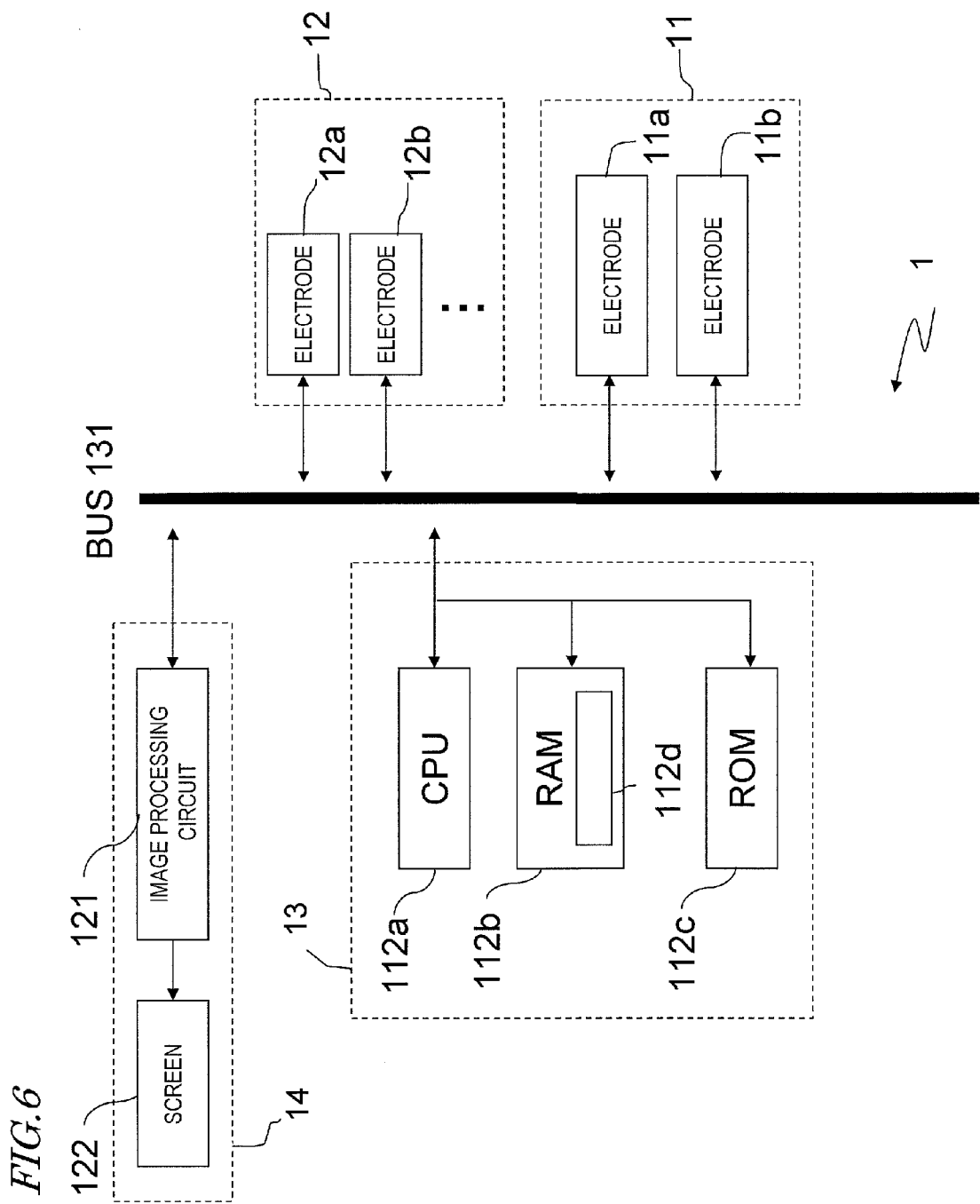
FIG. 6 is a hardware construction diagram of the electroencephalogram interface system 1.

FIG. 4 shows the functional block construction of an electroencephalogram interface system 1 according to the present embodiment. FIG. 5 shows an exemplary device shape of the electroencephalogram interface system 1. FIG. 6 shows an exemplary hardware construction of the electroencephalogram interface system 1.

As shown in FIG. 4, the electroencephalogram interface system 1 includes an ear electrode portion 11, a facial electrode portion 12, an electroencephalogram measurement and determination section 13, and an output section 14. In FIG. 4, the user 10 is illustrated for convenience of explanation.

As shown in FIG. 5, the names of respective portions of an HMD are similar to those of eyeglasses. Hereinafter, any portion that hangs on an ear of the user 10 to fix the HMD body will be referred to as an "endpiece portion 21". Any portion that comes in contact with the nose of the user 10 to support the HMD body will be referred to as a "nose pad portion 24". A portion which supports and fixes an output section 14 which is disposed before either eyeball of the user 10 will be referred to as a "rim portion 23". A portion connecting and supporting the rim portions 23 in front of both eyes will be referred to as a "bridge portion 25". A portion connecting and supporting each rim portion 23 and each endpiece portion 21 will be referred to as a "temple portion 22".

The electroencephalogram interface system 1 is realized as an eyeglass-type wearable device. The ear electrode portion 11 is provided in the ear periphery of the user, and the facial electrode portion 12 is provided on or around the face of the user. More specifically, the ear electrode portion 11 is provided inside an endpiece portion 21 of the eyeglasses, so as to be in contact with the ear periphery on one side of the face of the user 10. The facial electrode portion 12 is disposed at a position on the nose pad portion 24 where the HMD is in contact with the skin of the user's face. Note that the facial electrode portion 12 may be disposed on a temple portion 22 or a rim portion 23 of the eyeglasses. The electroencephalogram measurement and determination section 13 is disposed on the bridge portion 25 of the HMD. The electroencephalogram measurement and determination section 13 measures an electroencephalogram from a difference in potential between the ear electrode portion 11 and the facial electrode portion 12, and determines whether an electroencephalogram is being measured or not. If no electroencephalogram is being measured, it outputs a result of determination (signal) indicating that fact to the output section 14. If an electroencephalogram is measured, the electroencephalogram measurement and determination section 13 determines which menu item the user 10 wishes to execute, based on the electroencephalogram. This process will be described later.

The output section 14 has a function of providing a video output. The output section 14 is disposed in front of an eye of the user, at a lens portion of the eyeglasses. Based on the result of determination by the electroencephalogram measurement and determination section 13, the output section 14 displays information corresponding to that result of determination. For example, if no electroencephalogram is measured, the output section 14 may display a message "HMD is shifted. Please adjust.", and indicate an alarm for prompting the user to place the electrodes in proper positions. On the other hand, if an electroencephalogram is measured, the output section 14 sequentially highlights a plurality of menu items. Based on such highlight indication as a starting point, the electroencephalogram measurement and determination section 13 is able to determine which menu item the user 10 wishes to select. Moreover, the output section 14 displays a result of executing a process corresponding to the selected menu item.

Hereinafter, by mainly describing the operation of the electroencephalogram measurement and determination section 13, the fundamental functions of the electroencephalogram interface system will be described.

When an electroencephalogram is being measured, the electroencephalogram measurement and determination section 13 measures an electroencephalogram from a difference in potential between the ear electrode portion 11 and the facial electrode portion 12, and out of this, extracts 200 to 400 ms of the electroencephalogram of the user 10 based on the timing of presenting a visual stimulation at the output section 14 (e.g., highlight indication of a menu item) as a starting point, so as to determine a menu item which has been selected by the user from a characteristic signal thereof. Then, the electroencephalogram measurement and determination section 13 outputs the result of determination. This electroencephalogram is also referred to as a "P300 component of the event-related potential".

Visual stimulations are also utilized for purposes other than the aforementioned highlighting of menu items.

For example, visual stimulations are also utilized for determining correctness/incorrectness of the resultant selected menu item. More specifically, when a fed back result is presented as a visual stimulation, an electroencephalogram from 400 to 700 ms is extracted based on the timing of presenting the visual stimulation as a starting point. From this electroencephalogram, it is possible to determine whether the presented result is what was anticipated or incorrect. (MORIKAWA, ADACHI, "JISHOKANRENDENI WO MOCHIITA UZABIRITI HYOKASHUHOU" or "Developing Usability Testing Method Based on Event-Related Brain Potential", Matsushita Technical Journal (currently, Panasonic Technical Journal), Vol. 53, No. 1, pp. 51-55, October 2007)

Figure 23:
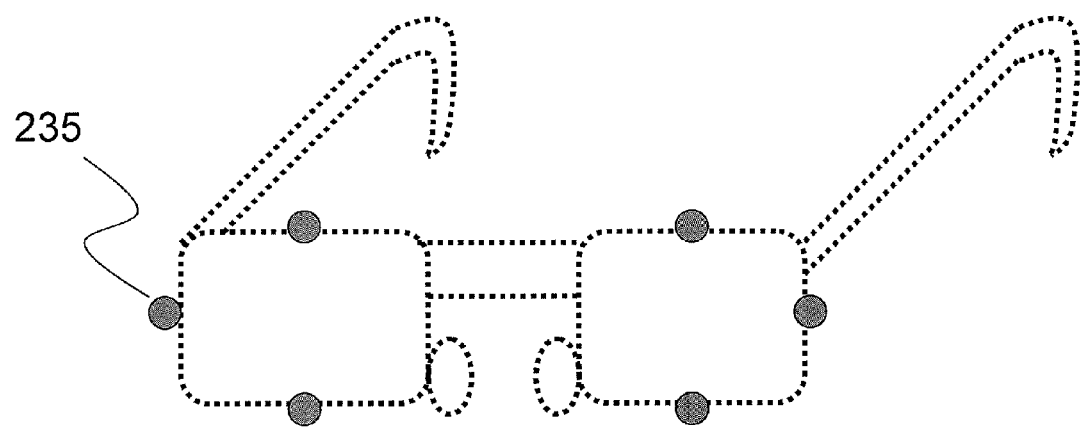
FIG. 23 is a diagram showing another exemplary construction of an electroencephalogram interface system.
Figure 24:
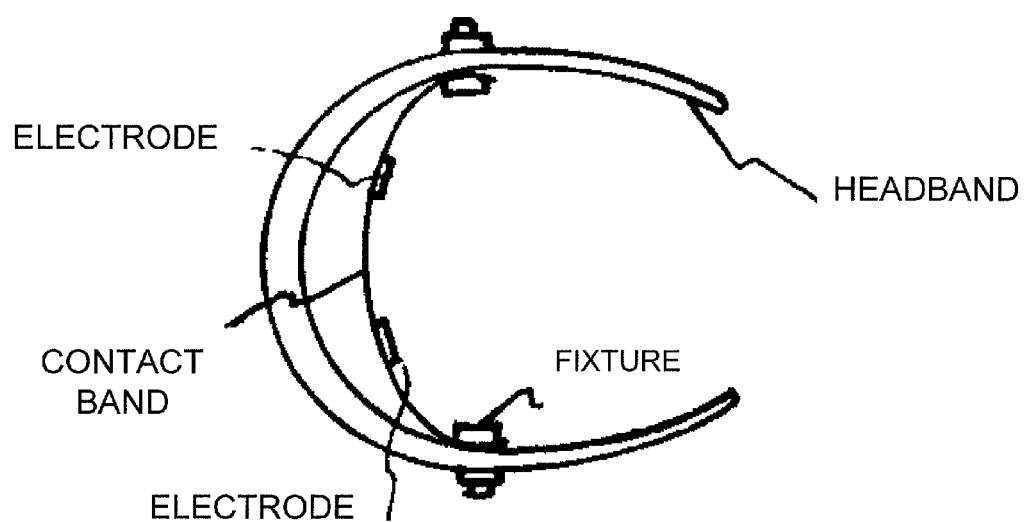
FIG. 24 is a diagram showing the construction of a conventional device for electroencephalogram electrode attachment.

Moreover, visual stimulations are also utilized for determining an amount of attention to the peripheral visual field while driving an automobile or walking. FIG. 23 shows an exemplary construction of an electroencephalogram interface system for determining an amount of attention. This electroencephalogram interface system has a plurality of LEDs (e.g., LEDs 235) around the lens portions. Each LED is placed so as to be visible in the peripheral visual field of a user. The electroencephalogram interface system activates visual stimulations (LEDs) in the peripheral visual field of the user at random intervals, and extracts an electroencephalogram (P300 component) of the user at 200 to 400 ms from the timing of activation. From the level of this P300 component, the electroencephalogram interface system is able to determine how much attention was being directed to the peripheral visual field.

In the following description, highlight indication of a menu item will be taken as an example.

By acquiring an event-related potential since the moment that a menu item was highlighted, a user's response to the highlighted menu item is obtained.

The electroencephalogram measurement and determination section 13 checks the waveform data of a measured event-related potential against a determination criterion which is stored in the determination criterion database, and determines whether the user wishes to select that menu item or not. Experimental results which have been performed for various test subjects are stored in the determination criterion database, and are prestored in the electroencephalogram measurement and determination section 13, for example.

Specifically, a plurality of menu items are sequentially highlighted to a test subject who wishes to select a certain menu item, and an event-related potential is acquired at the timing of highlighting. Then, averages are respectively taken of waveform data A of event-related potentials when a menu item meant to be selected is highlighted and waveform data B of event-related potentials when a menu item not meant to be selected is highlighted, and each is stored in a determination criterion database. Using each of waveform data A and waveform data B as a template, the electroencephalogram measurement and determination section 13 may determine the one waveform that the waveform of the event-related potential of the user 10 (a manipulator of the electroencephalogram interface system 1) is closer to, i.e., the closest waveform, based on a Mahalanobis distance.

The Mahalanobis distance indicates a distance from the center of gravity of a group, by taking into consideration the variance and covariance of data. Therefore, a determination using the Mahalanobis distance provides a higher distinction ability than making a determination through simple threshold processing. As a result, the menu item which the user wishes to select can be determined.

Through such processes, without making a button manipulation or the like, selection of a menu item is realized on the basis of an electroencephalogram.

FIG. 6 is a hardware construction diagram of the electroencephalogram interface system 1.

The ear electrode portion 11 and the facial electrode portion 12 worn on the face are connected to a bus 131 in order to perform exchanges of signals with the electroencephalogram measurement and determination section 13. The electroencephalogram measurement and determination section 13 includes a CPU 112$a$, a RAM 112$b$, and a ROM 112$c$. The CPU 112$a$ reads a computer program 112$d$ which is stored in the ROM 112$c$ onto the RAM 112$b$, where the computer program 112$d$ is laid out and executed. In accordance with the computer program 112$d$, the electroencephalogram measurement and determination section 13 switchably executes a process of when electroencephalogram data is detected or a process of when electroencephalogram data is not detected. The ROM 112$c$ may be a rewritable ROM (e.g., an EEPROM).

A display 14, which is the output section 14, includes an image processing circuit 121 and a screen 122. In accordance with a result from the CPU 112$a$, the image processing circuit 121 outputs a video signal, e.g., for displaying a selected content video, to the screen 122.

The aforementioned display 14 is illustrated as having the image processing circuit 121 and the screen 122 because control of an AV device is contemplated. However, depending on the modality type of the device to be controlled, the image processing circuit 121 and the screen 122 may be replaced by an audio processing circuit, a loudspeaker, and the like.

The aforementioned computer program is distributed on the market in the form of a product recorded on a storage medium such as a CD-ROM, or transmitted through telecommunication lines such as the Internet. The electroencephalogram measurement and determination section 13 and the image processing circuit 121 may be implemented as a piece of hardware (e.g., a DSP) consisting of semiconductor circuitry having a computer program incorporated therein.

Next, as one feature of the present embodiment, positioning of the electrodes will be described in more detail.

Figure 1B:
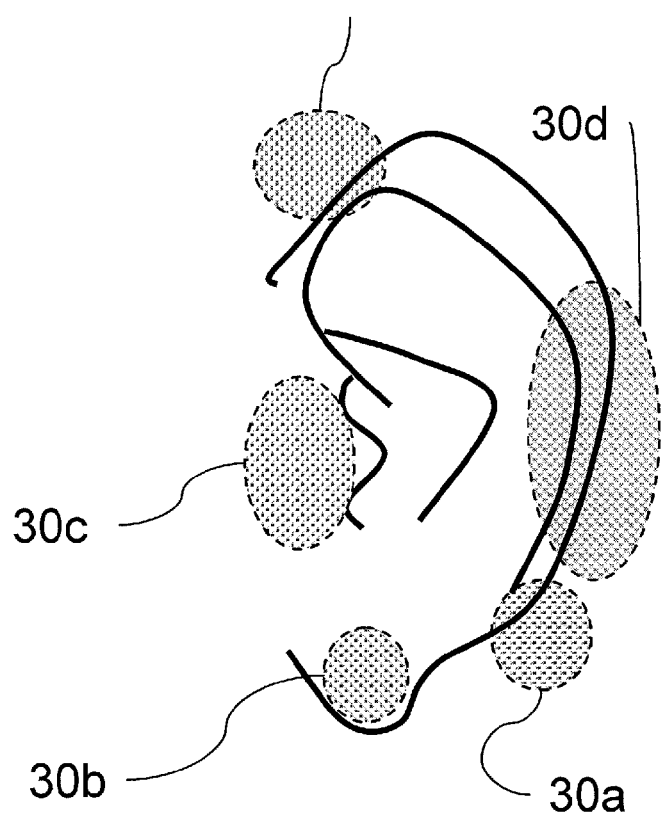

As shown in FIG. 1B, the ear electrode portion 11 needs to be worn within the range of the ear periphery of the user 10. When an eyeglasses shape is taken into consideration, by placing an electrode at the inner tip end of an endpiece portion 21 of the eyeglasses, the electrode is allowed to achieve contact with the skin of the user 10 at the ear root posterior or the mastoid.

The example of FIG. 5 illustrates a case where the ear electrode portion 11 is placed inside the endpiece portion 21 on the right side. However, according to the results of the experiment of FIG. 3, there is no substantial difference in accuracy depending on whether the reference electrode is at a right or left position. Therefore, a high-accuracy electroencephalogram measurement can be similarly achieved also by placing the ear electrode portion 11 at the inside of the endpiece portion 21 on the other side (left side).

The facial electrode portion 12 is to be worn within the range of the face of the user 10 as shown in FIG. 1A. In a normal eyeglass-type shape, within the face of the user 10, portions that are strongly in contact with the HMD are positions from the ear-root superior portions to the temples, and the nasion, of the user 10. At the temples of the user 10, the HMD is fixed so as to sandwich the head of the user 10 and not wobble to the right or left, such that the HMD mass is supported at the ear-root superior portions and the nasion of the user 10.

The output section 14 is composed of a liquid crystal display device or the like. Therefore, the output section 14 can be considered as the heaviest and largest element of hardware composing the electroencephalogram interface system 1 (FIG. 6). When an HMD shape is taken into consideration, the heaviest output section 14 rests on a lens, whereas the constituent elements having large volumes are concentrated in the neighborhood of the lenses (front). Therefore, the HMD mass concentrates on the front, such that the center of gravity leans toward the front, so that presumably most of the mass of the HMD is supported at the face front (nasion) position of the user 10.

Therefore, by placing the facial electrode portion 12 at the tip end of the nose pad portion 24, it is ensured that the mass of the HMD is supported by the facial electrode portion 12, such that the facial electrode portion 12 is strongly in contact with a position on a side of the nasion of the user 10, under the weight of the HMD.

Therefore, no excessive pressure acts on the facial electrode portion 12 beyond what is needed for supporting the HMD, and the facial electrode portion 12 is supported by the force of supporting the HMD, which makes it unlikely for the facial electrode portion 12 to be shifted.

Moreover, adopting a structure such that the endpiece portions are in contact with the ear-root superior portions of the user 10 and are caught on the ears of the user 10 provides the following advantages. Even when the face of the user 10 is tilted frontward, the endpiece portions will alleviate the frontward shift of the HMD, and since the facial electrode portion 12 is fixed onto the face of the user 10 with a moderate pressure, shifting and lifting of the facial electrode portion 12 can be prevented. Therefore, the endpiece portions need to have a bent shape for being caught by the ears.

As described above, by disposing the electrodes at positions where the mass of the HMD is supported, it becomes unnecessary to fix the electrodes with excessive pressuring as is done by a hair band, whereby the user's burden of wearing the HMD can be reduced.

By disposing the facial electrode at the nasion, it is ensured that the electrode is located below the straight line connecting the internal canthus and the external canthus, whereby the influence of blink noise is suppressed. This enables clear electroencephalogram measurements with few artifacts.

Furthermore, by disposing the ear electrode portion on the same side as the facial electrode portion with respect to the straight line 233 connecting the internal canthus and the external canthus (FIG. 23), artifacts due to eye movement along the vertical direction can be reduced. For example, by disposing the ear electrode portion at the mastoid 30a or the opisthotic 30d (FIG. 1), the ear electrode portion will be disposed on the same side as the facial electrode portion (which in itself is disposed at the nasion) with respect to the straight line 233 connecting the internal canthus and the external canthus. Since the ear electrode portion and the facial electrode portion are disposed on the same side, the influence of a potential when an eyeball moves in an up-down direction occurs almost equally in the ear electrode portion and in the facial electrode portion. Therefore, when measuring a potential difference between the ear electrode portion and the facial electrode portion, the influence of the electro-oculographic potential along the up-down direction is canceled, thus enabling electroencephalogram measurements with little noise.

Although the present embodiment illustrates an example where the facial electrode portion 12 is disposed on the nose pad portion, other electrode positioning is also possible. With reference to FIG. 7 and FIG. 8, other examples of electrode positioning will be described.

Figure 7A:
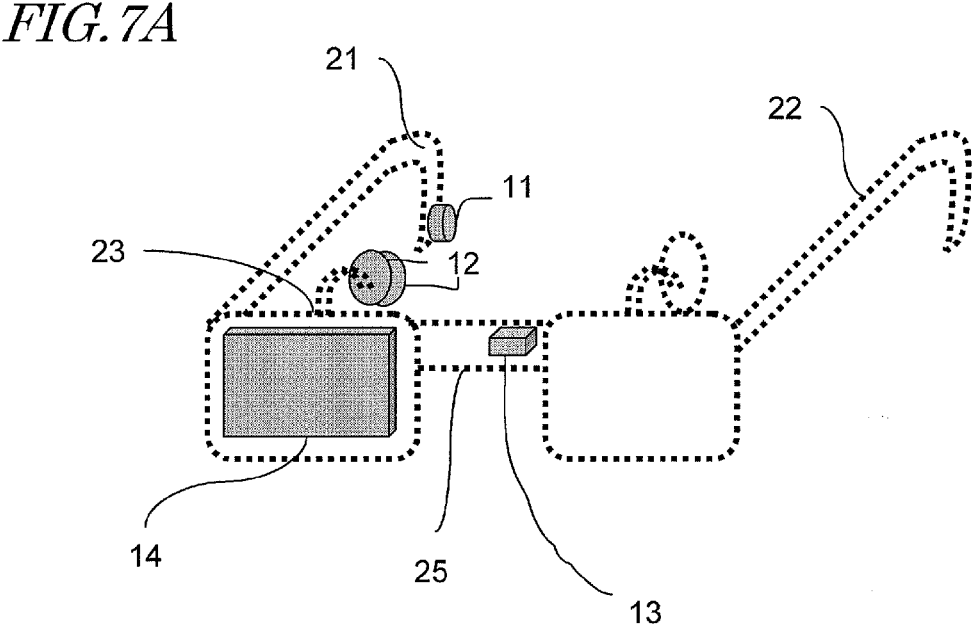
FIG. 7A is a diagram showing an example where a facial electrode portion 12 is disposed on a rim portion 23 of an HMD.
Figure 7B:
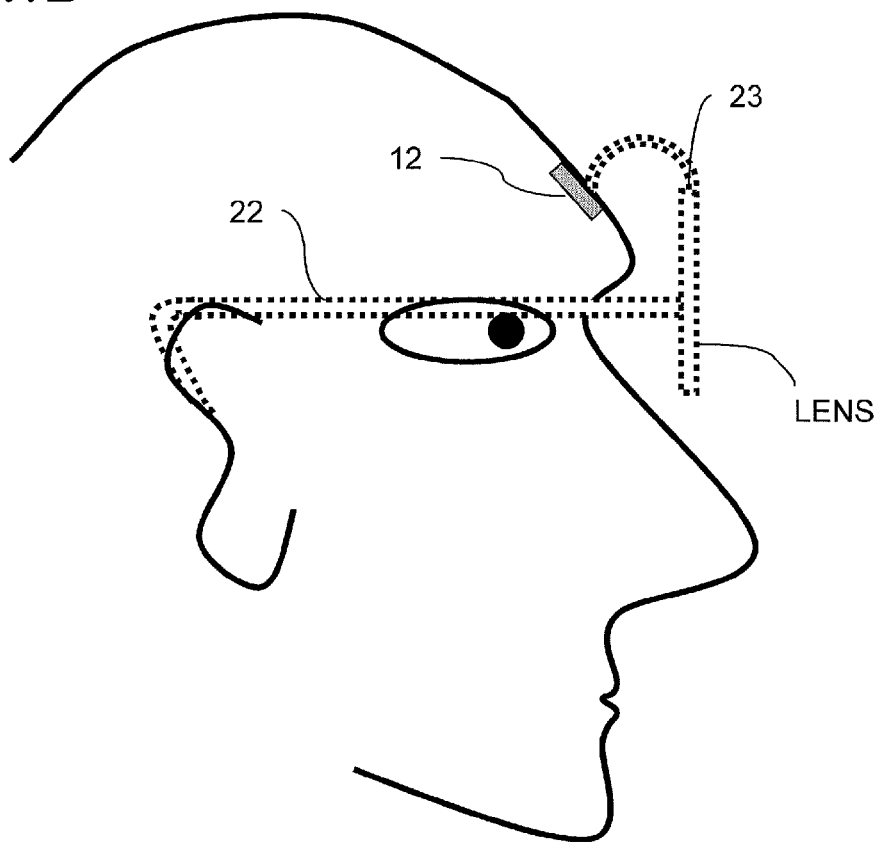
FIG. 7B is a diagram showing how the HMD-type electroencephalogram interface system 1 shown in FIG. 7A may be worn by a user 10.

FIG. 7A shows an example of disposing the facial electrode portion 12 on a rim portion 23 of the HMD. This is an example where, through alteration of the rim portion 23 of the HMD, the facial electrode portion 12 is disposed at a position where the rim portion 23 comes in contact with an eye-socket upper edge of the user 10, thus allowing the HMD mass to be supported at the position of the eye-socket upper edge of the user. FIG. 7B shows how the electroencephalogram interface system 1 shown in FIG. 7A may be worn by the user 10.

Figure 8A:
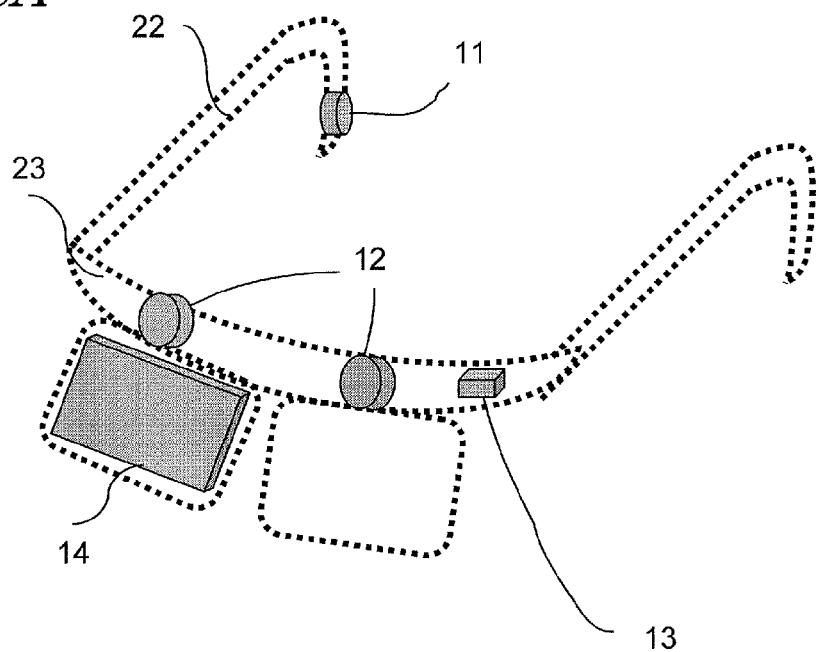
FIG. 8A is a diagram showing an example where a further altered rim portion 23 of an HMD allows facial electrode portions 12 to be disposed thereon.
Figure 8B:
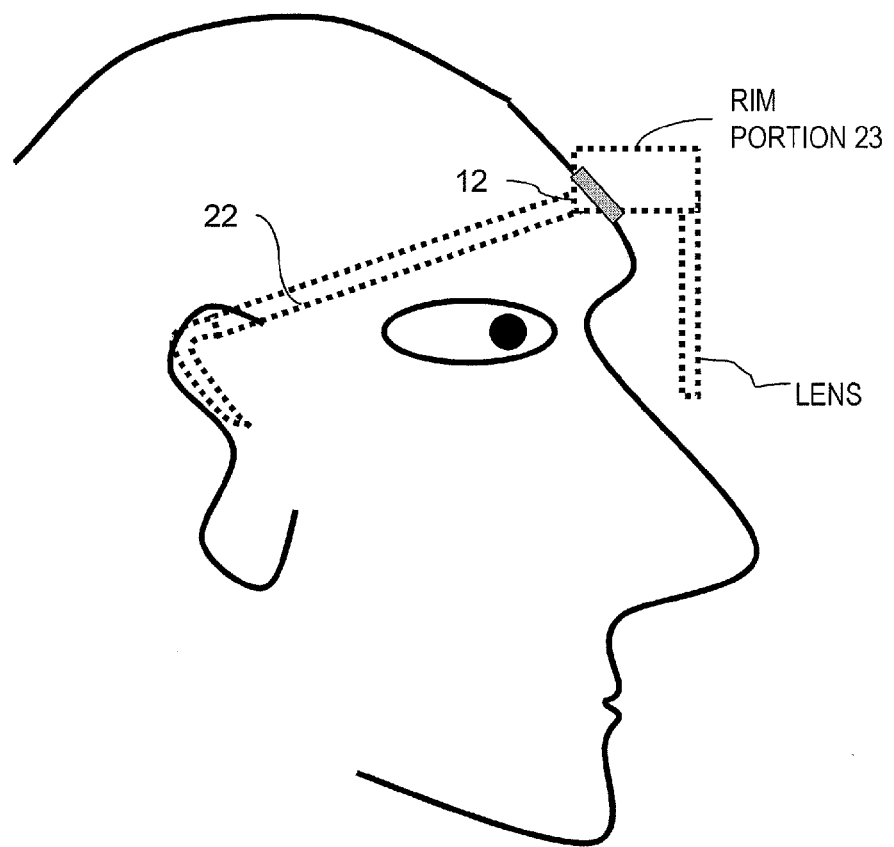
FIG. 8B is a diagram showing how the HMD-type electroencephalogram interface system 1 shown in FIG. 8A may be worn by a user 10.

FIG. 8A shows an example where a further altered rim portion 23 of an HMD allows facial electrode portions 12 to be disposed thereon. This is an example where the rim portion 23 and the bridge portion 25 are integrated to realize a shape such that the endpiece portions 21 and the rim portion 23 sandwich the head's user so as to fix the HMD, thus allowing the mass of the HMD front to be supported by the rim portion 23. FIG. 8B shows how the electroencephalogram interface system 1 shown in FIG. 8A may be worn by the user 10. In this case, too, the facial electrode portions 12 disposed on the rim portion 23 are fixed by the mass of the HMD acting on the rim portion 23, and thus is unlikely to be shifted.

Figure 9:
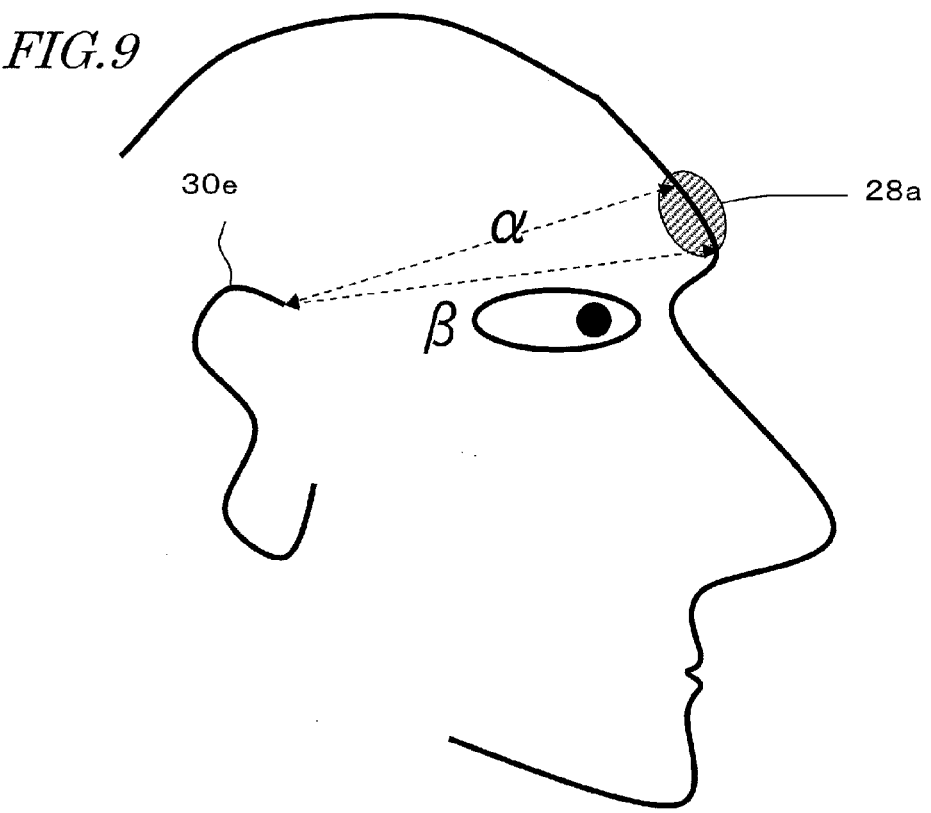
FIG. 9 is a diagram showing a relative distance from an ear-root superior portion to an eye-socket upper edge of a human face.

FIG. 9 shows a relative distance from an ear-root superior portion to an eye-socket upper edge on a human face. In the shape of a human face, the distance from the ear-root superior portion 30e to the eye-socket upper edge 28a decreases away from the lower end, and toward the upper end, of the eye-socket upper edge 28a. That is, between the distance $\alpha$ from the ear-root superior portion 30e to the upper end of the eye-socket upper edge 28a and the distance $\beta$ from the ear-root superior portion to the lower end of the eye-socket upper edge 28a, the former distance $\alpha$ is the shorter.

Therefore, by ensuring that the distance from the root of the endpiece portion 21 to the facial electrode portion 12 in the electroencephalogram interface system 1 shown in FIG. 7A is equal to or greater than $\alpha$ but less than $\beta$, the roots of the endpiece portions will be caught on the ears of the user 10, so that the endpiece portions and the facial electrode portion will be fixed onto the head of the user 10 in a manner of sandwiching the head. Thus, the HMD needs to have endpiece portions whose tip ends are bent for being caught by the ear-root superior portions. The advantage of ensuring that the distance from the root of each endpiece portion 21 to the facial electrode portion 12 is equal to or greater than $\alpha$ but less than $\beta$ also applies to the example of FIG. 8.

By being worn in the aforementioned manner, most of the HMD mass is supported by the electrode at the face front, as in the case of the electroencephalogram interface device shown in FIG. 5, so that the facial electrode 12 will be pressed against the user 10 with no excessive pressuring.

With the shape of FIG. 5, FIG. 7, or FIG. 8, an electroencephalogram interface device can be constructed such that the facial electrode portion 12 is fixed through utilization of the HMD mass and the electrodes are unlikely to be shifted.

Furthermore, in the case where the HMD mass is supported at the rim portions 23 as described above, omitting the nose pad portion(s) 24 of the HMD will prevent dispersion of the HMD mass. By omitting the nose pad portion(s) 24 so that the HMD mass concentrates on the eye-socket upper edges 28a of the user, the HMD will be firmly supported by the facial electrode portion(s) 12 disposed on a rim portion 23, thus further preventing a shift.

Although the present embodiment illustrates an example where the electroencephalogram measurement and determination section 13 is disposed on the bridge portion 25 or the rim portion 23 of the HMD, the present invention also encompasses disposing the electroencephalogram measurement and determination section 13 in any portion of the position (e.g., a temple portion 22 or an endpiece portion 21) of the HMD to account for the balance of the HMD mass.

Figure 10:
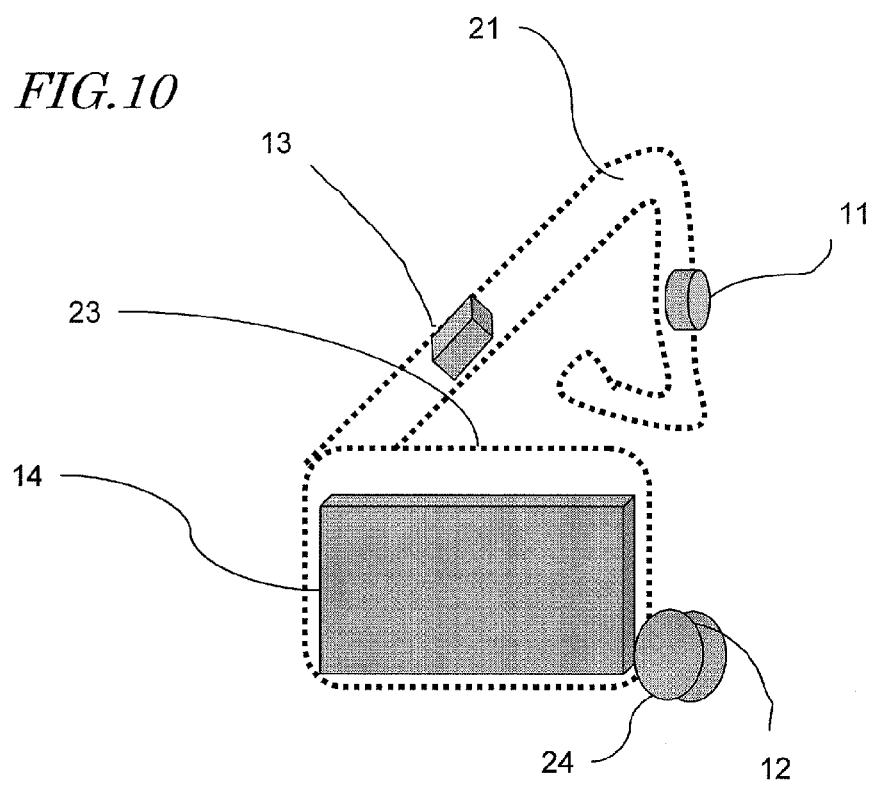
FIG. 10 is a diagram showing an exemplary construction of the electroencephalogram interface system 1 to be worn on one side of the face.

FIG. 10 shows an exemplary construction of the electroencephalogram interface system 1 to be worn on one side of the face. Since the firm support for the HMD provided by the ear electrode portions 11 and the facial electrode portion 12 will be maintained, even the illustrated construction to be worn on one side of the face can be worn on the user's head for a long time without much chance of a shift.

Embodiment 2

In Embodiment 1, as shown in FIG. 5, FIG. 7, FIG. 8, and FIG. 10, a construction was illustrated where endpiece portions are hung on the ear-root superior portions so that the facial electrode portion(s) 12 which is in contact with the face of the user 10 supports the HMD mass, thus fixing the HMD in a manner of sandwiching the head with the endpiece portions and the facial electrode portion(s) 12. In particular, the HMD examples of FIG. 7 and FIG. 8 utilize a difference between the distance α from an ear-root superior portion to the upper end of an eye-socket upper edge and the distance β from the ear-root superior portion to the lower end of the eye-socket upper edge as shown in FIG. 9, thus fixing the HMD in a manner of sandwiching the head of the user 10.

However, the shapes of the face and the head differ from person to person, and it is also possible for the distances α and β shown in FIG. 9 to differ depending on each individual. Therefore, sandwiching of the user head with the endpiece portions and the facial electrode portion 12 may not work in some cases.

Moreover, even if the user himself or herself may feel that the HMD is worn fine, the facial electrode portion abutting with the face may become shifted in position, under the influences of the mass of the HMD itself and user motions. When the electrode becomes shifted in such a manner, it is difficult for the user 10 to notice the shift of the electrode because the user 10 cannot use his or her own eyes to directly see how the electrode is shifted. Therefore, even if the user 10 operates the electroencephalogram interface on the belief that the HMD must be correctly worn, the distinction ratio may be too low for successful use.

In the present embodiment, the HMD is fixed in a manner of reducing the shift of the facial electrode portion 12 regardless of the aforementioned face and/or head shape differences from person to person, and when the position of the facial electrode does become shifted under the influences of the posture or motion of the user 10, an alarm sound is presented to the user 10, thus providing an HMD-type electroencephalogram interface device capable of stable electroencephalogram measurement.

Figure 11A:
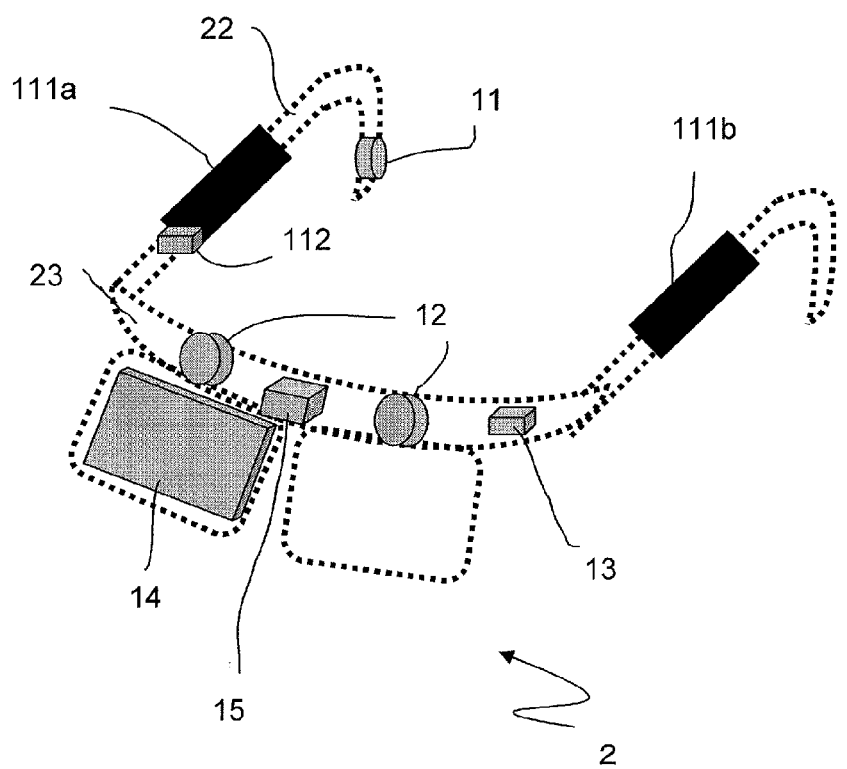
FIG. 11A is a diagram showing the construction of an electroencephalogram interface system 2 according to the present embodiment.
Figure 11B:
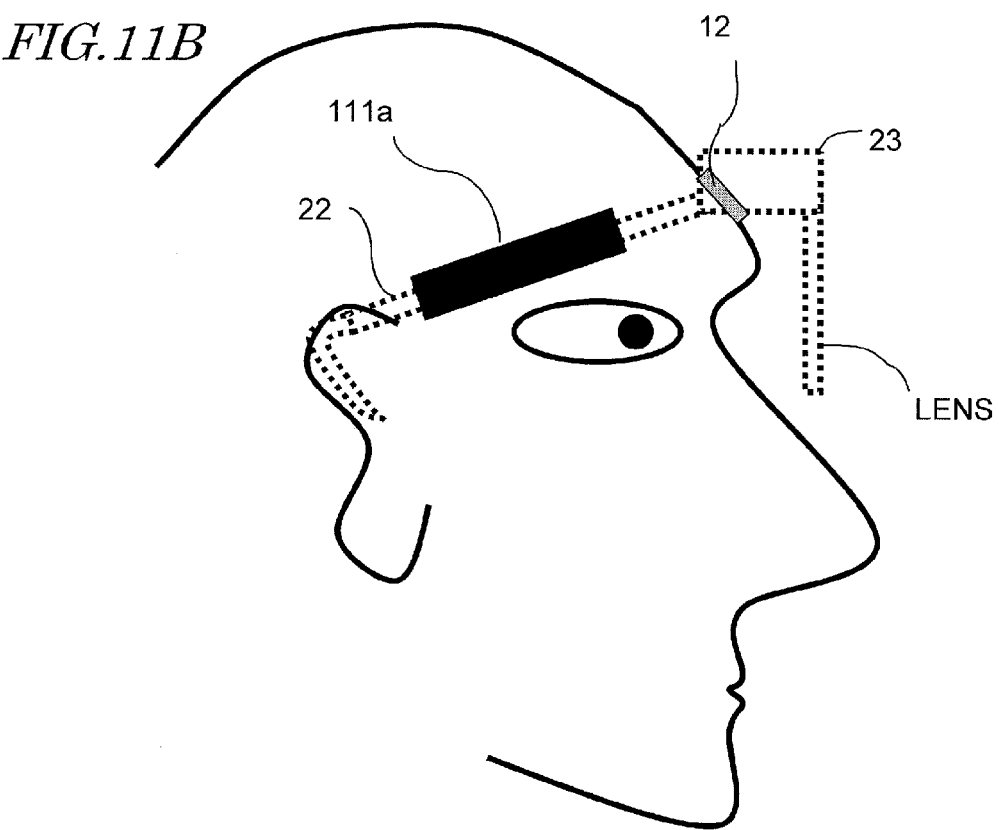
FIG. 11B is a diagram showing the position of the electroencephalogram interface system 2 when being worn.
Figure 12:
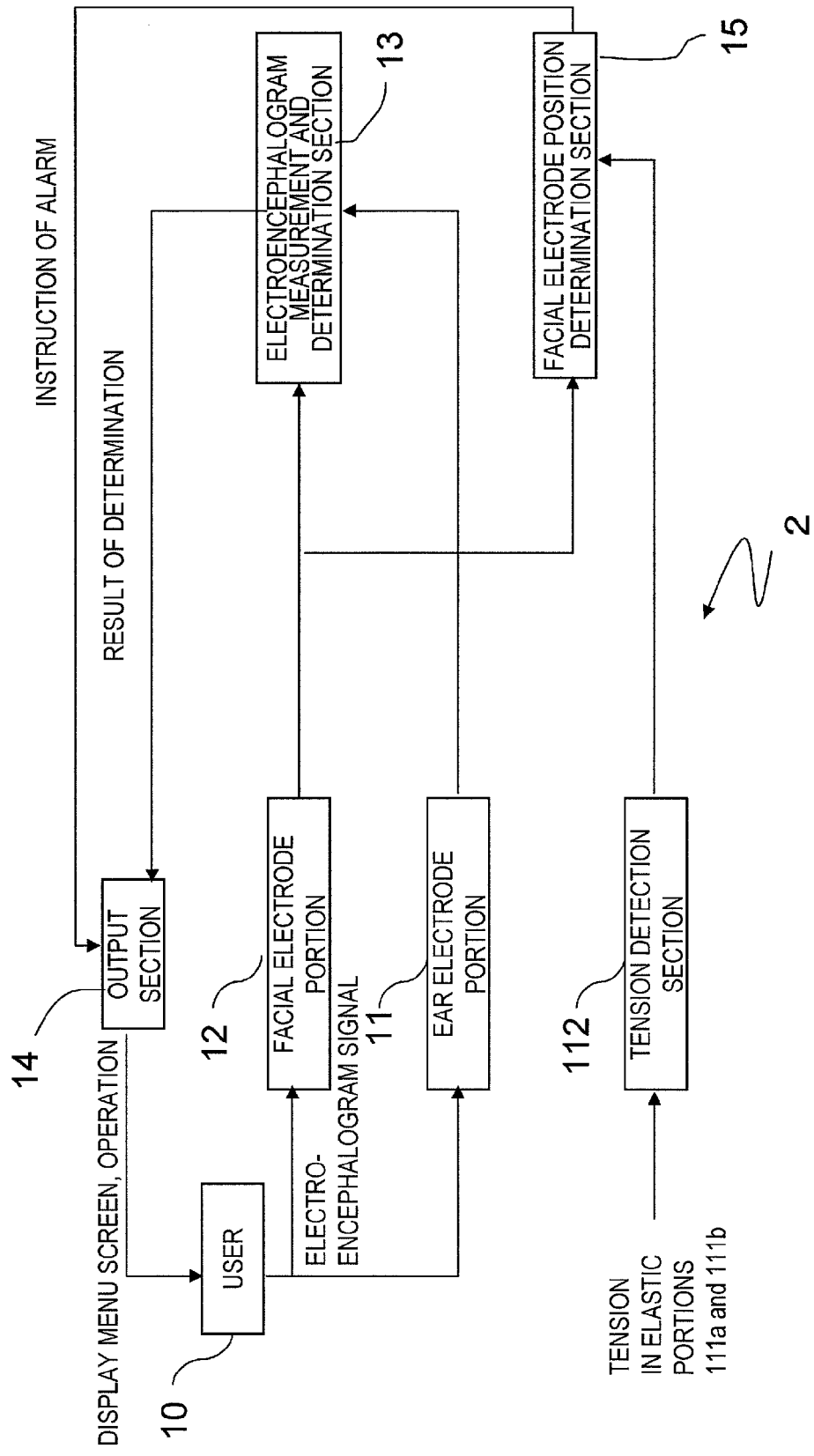
FIG. 12 is a diagram showing a functional block construction of the electroencephalogram interface system 2.

With reference to FIG. 11 and FIG. 12, an example of an electroencephalogram interface device which can cope with individual differences in the distances α and/or β in FIG. 9 will be described.

FIG. 11A shows the construction of an electroencephalogram interface system 2 according to the present embodiment, whereas FIG. 11B shows the position of the electroencephalogram interface system 2 when being worn. In addition to the construction of the electroencephalogram interface system 1 of Embodiment 1, elastic portions 111a and 111b for adjusting the lengths of the temple portions, a tension detection section 112 for detecting whether tension exists in the elastic portions or not, and a facial electrode position determination section 15 for determining whether the facial electrode portion 12 is worn at the correct position of the face of the user 10 are newly provided.

The elastic portions 111a and 111b are provided at the temple portions 22, and allow the lengths of the temple portions 22 to be adjusted. The elastic portions 111a and 111b are each made of an elastic body such as a spring or rubber. In its interior, the elastic portion 111a includes a signal line for transmitting a signal (electroencephalogram signal) which is detected by the ear electrode portion 11. Even if the elastic portion 111a is made of an insulative substance, an electroencephalogram signal which is measured by the ear electrode portion 11 can be transmitted to the facial electrode position determination section 15 and the electroencephalogram measurement and determination section 13.

The tension detection section 112 and the facial electrode position determination section 15 will be described with reference to FIG. 12.

FIG. 12 shows the functional block construction of the electroencephalogram interface system 2 for the embodiment 2. Hereinafter, with reference to FIG. 12, the constituent elements of the electroencephalogram interface system 2 will be described. The tension detection section 112 is a sensor which is connected to the elastic portion 111a and measures the level of tension acting on the elastic portion 111a. Although no tension detection section is provided for the elastic portion 111b in this example, a tension detection section may be provided for each of the elastic portions 111a and 111b. Hereinafter, the elastic portion 111a with the tension detection section 112 connected thereto will be simply referred to as the "elastic portion 111".

The ear electrode portion 11 and the facial electrode portions 12 are worn at an ear periphery and on the face of the user 10, respectively, for measuring an electroencephalogram of the user 10. A measured electroencephalogram signal is sent to the facial electrode position determination section 15 and the electroencephalogram measurement and determination section 13.

The facial electrode position determination section 15 is disposed on a temple portion, rim portion, or the like of the HMD, and determines whether the facial electrode portions 12 are worn at the correct positions of the forehead of the user 10 or not by using the measured electroencephalogram signal as an input. If the facial electrode position determination section 15 determines that they are not correctly worn, it instructs the output section 14 to output an alarm for the user 10. The detailed flow of processes will be described later.

The electroencephalogram measurement and determination section 13 instructs the output section 14 to present a visual stimulation to the user 10. From the measured electroencephalogram signal, the electroencephalogram measurement and determination section 13 extracts an event-related potential based on the timing of presenting the visual stimulation as a starting point, determines an option which the user wishes to select by using a characteristic signal (e.g., an N100 component or P300 component) contained in the event-related potential, and outputs a result of determination to the output section 14.

The output section 14 presents a visual stimulation to the user 10 and displays the selection result, presents an alarm sound if the HMD is poorly worn, as well as outputting a menu selection screen, video/audio, and the like. The output section 14 is composed of a display, a loudspeaker, and the like.

The hardware configuration of the electroencephalogram interface system 2 according to the present embodiment is also similar to that of FIG. 6. However, a sensor must be added as the tension detection section 112. As for the facial electrode position determination section 15, a CPU, an RAM, or the like may be separately provided, or the CPU 112a shown in FIG. 6 (as composing the electroencephalogram measurement and determination section 13) may perform a process corresponding to the facial electrode position determination section 15 to function as the facial electrode position determination section 15.

Figure 13:
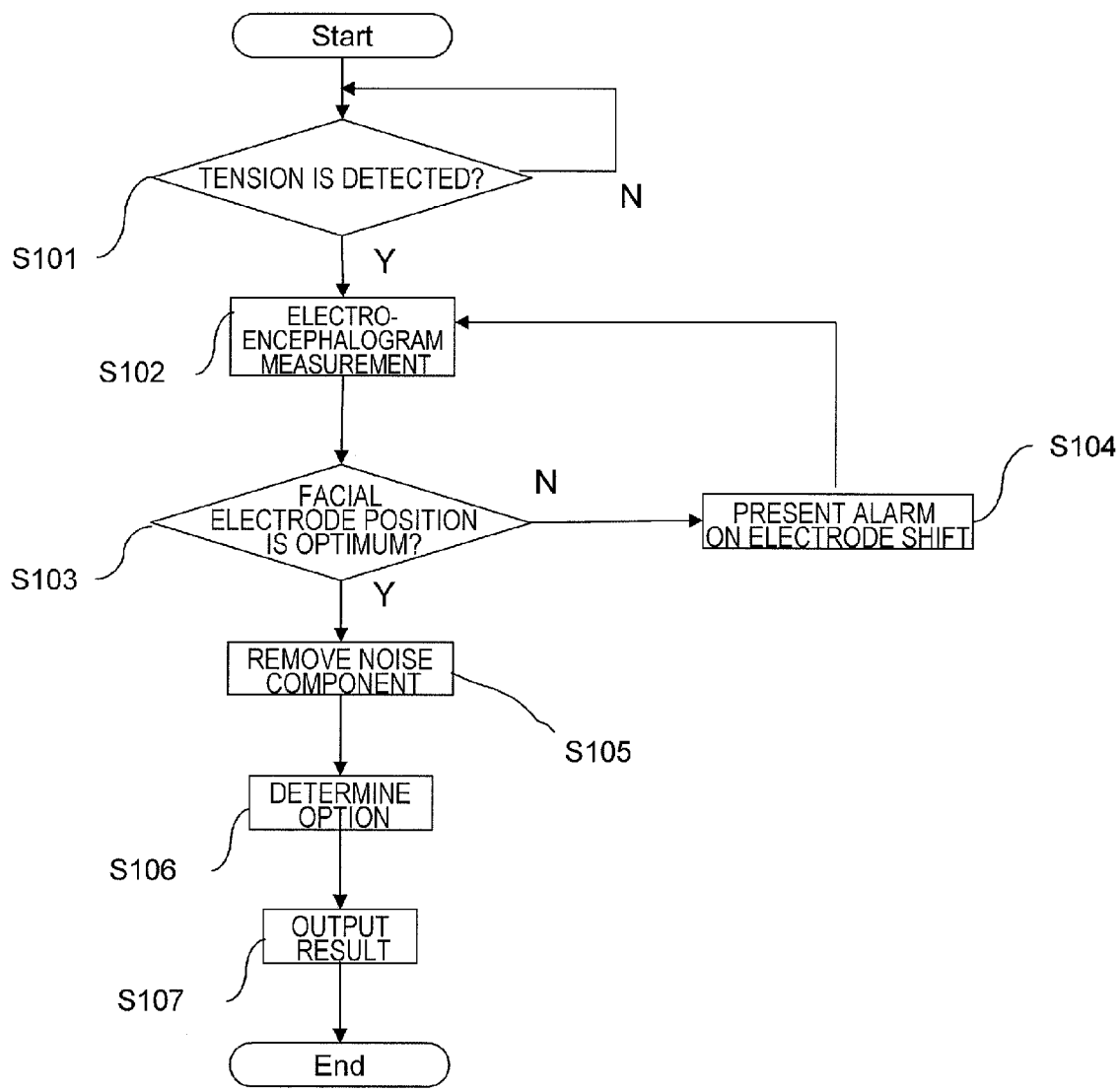
FIG. 13 is a flowchart showing a procedure of processing by the electroencephalogram interface system 2.

FIG. 13 shows a procedure of processing by the electroencephalogram interface system 2. With reference to FIG. 13, a flow of processes by the aforementioned blocks will be described.

At step S101, the tension detection section 112 monitors the elastic portion 111 to perform a measurement as to whether tension has occurred in the elastic portion 111. If the elastic portion 111 is composed of a spring, for example, by designing it so that the spring is in its shrunk state and that the temple portion has a short length, it is ensure that tension will always occur in the elastic portion 111 when the user 10 wears the HMD. Thus, the tension detection section 112 is able to know when the user 10 has put on the HMD by monitoring the tension in the temple portions 22.

The tension detection section 112 detects whether any tension has occurred or not. By being fixed to the temple portion at one end and fixed to the elastic portion 111 at the other end, the tension detection section 112 measures a tension occurring in the elastic portion 111. The force acting on the elastic portion 111 is compared against a threshold value (e.g., 0 (zero) newtons), and the point in time when the force applied to the elastic portion 111 exceeds the threshold value is detected as the timing when the HMD is worn by the user 10. The tension detection section 112 may be designed so that a tension measurement sensor always keeps measuring tension, or may be a circuit which determines occurrence of a tension exceeding the threshold value by having a switch that physically establishes connection when a tension occurs in the elastic portion 111.

Since the elastic portions 111a and 111b expand or contract, it becomes possible to support the varying length from the ear-root superior portion to the eye-socket upper edge of each user (distance α in FIG. 9).

After detecting the HMD being worn by the user 10, at step S102, the facial electrode position determination section 15 measures an electroencephalogram via the ear electrode portion 11 and the facial electrode portions 12. The electroencephalogram signal is output to the facial electrode position determination section 15 and the electroencephalogram measurement and determination section 13.

At step S103, from the measured electroencephalogram signal, the facial electrode position determination section 15 determines whether the positions of the facial electrode portions 12 as worn by the user 10 are at the correct positions or not. The method of determination will be described later.

If it is determined that the positions of the facial electrode portions 12 are not optimum, the process proceeds to step S104; if they are determined as optimum, the process proceeds to step S105.

At step S104, the facial electrode position determination section 15 gives an instruction to the output section 14 to present an alarm. For example, the facial electrode position determination section 15 may output to the output section 14 a video signal of an alarm to be displayed by the output section 14. Upon receiving this instruction, the output section 14 alarms the user 10 of an electrode shift, i.e., that the facial electrode portions are not in the correct positions. As an alarm of this electrode shift, the output section 14 may present an alarm sound via a loudspeaker, present an alarm screen via a display, etc., for example.

Thereafter, the facial electrode position determination section 15 again performs the facial electrode position determination of step S103, and alarming (step S104) and determination (step S103) are repeated until the positions of the facial electrode portions 12 are determined as optimum.

If the positions of the facial electrode portions 12 are determined to be the correct positions, then, at step S105, the electroencephalogram measurement and determination section 13 removes noise components such as blinks and electromyographic potentials from the electroencephalogram signal measured with the ear electrode portion 11 and the facial electrode portions 12. Removal of the noise component may be performed by, for example, deleting any portion of the electroencephalogram signal whose amplitude goes outside ±100 µV, using FFT to filter out any portion that is 30 Hz or more by regarding it as an electromyographic potential, or other methods.

At step S106, out of the electroencephalogram signal from which noise has been removed, the electroencephalogram measurement and determination section 13 cut outs an event-related potential based on the timing of presenting the visual stimulation (which is output by the output section 14) as a starting point. The electroencephalogram measurement and determination section 13 extracts event-related potentials corresponding to the presented stimulations of a plurality of options, and determines which option has been selected by the user 10, based on characteristic signals of the event-related potentials.

As a method of determination, for example, the level of a P300 component (a zone average potential from 200 ms to 400 ms, where the point of stimulation presentation is defined as 0 ms) of the event-related potential for each option may be compared, and a stimulation of an option having the largest P300 component may be determined as the option selected by the user 10. The result of determination is output to the output section 14.

At step S107, the output section 14 feeds back the result of determination to the user 10 by utilizing a display device such as a liquid crystal screen. Moreover, it outputs a video and/or audio in accordance with the contents of the option selected by the user 10.

Note that the process of step S101 may be omitted. The processes of step S102 and subsequent steps may be performed by regarding the timing of activating the power of the HMD as the timing when the user 10 has put on the HMD. Alternatively, the processes of step S102 and subsequent steps may be performed on the supposition that the user 10 is wearing the HMD whenever the electroencephalogram interface system 2 is operating.

Figure 14:
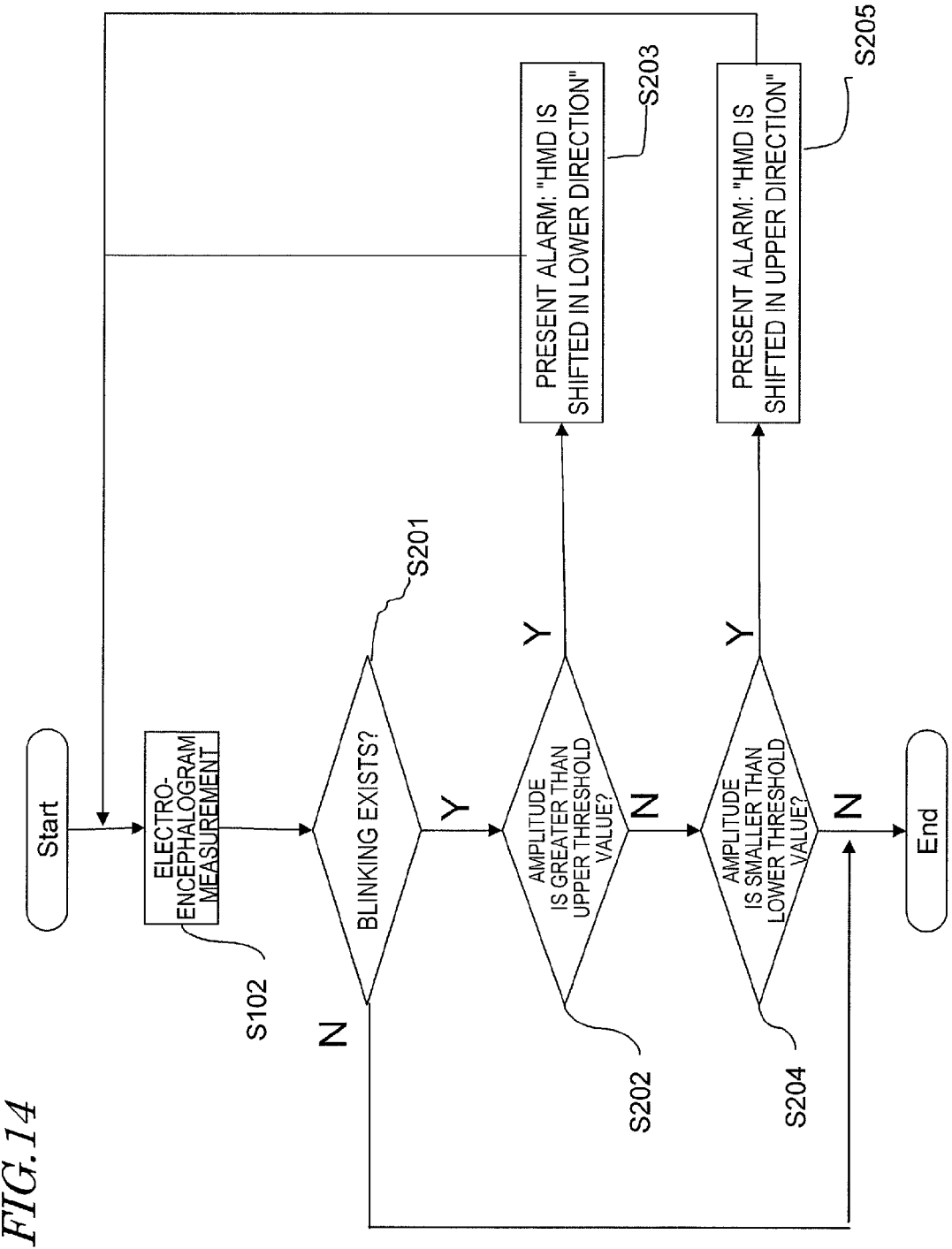
FIG. 14 is a flowchart showing a detailed procedure of processes by a facial electrode position determination section 15 shown at steps S102, step S103, and step S104 of FIG. 13.

FIG. 14 shows a detailed procedure of processes by the facial electrode position determination section 15 shown at steps S102, step S103, and step S104 in FIG. 13.

At step S102, as in step S102 of FIG. 13, the facial electrode position determination section 15 measures an electroencephalogram with the electrode portion 11 and the facial electrode portions 12.

At step S201, the facial electrode position determination section 15 detects whether any signal associated with blinking is contained in the measured electroencephalogram signal. Details of the blink detection method are described below.

Figure 15A:
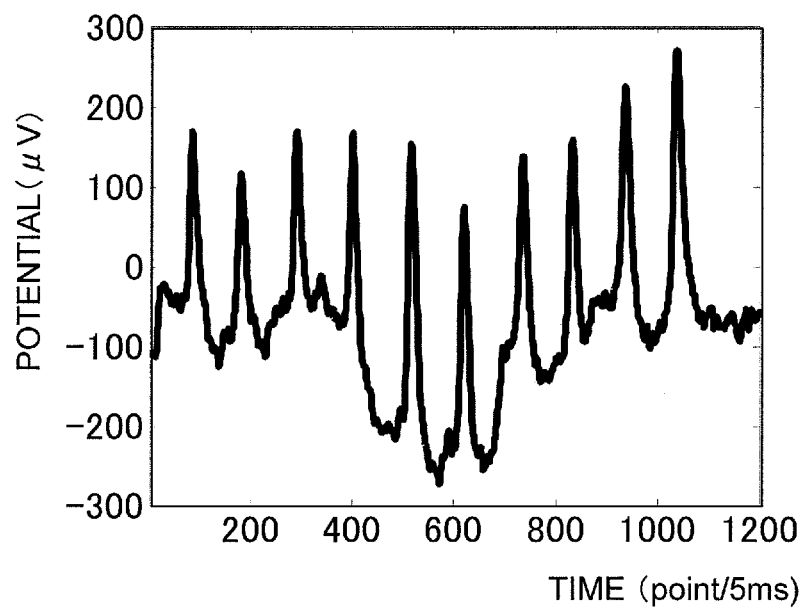
FIG. 15A is an exemplary diagram showing an electroencephalogram signal when blinks are made, with an ear electrode portion 11 being worn at the right mastoid and a facial electrode portion 12 being worn at the right eye-socket upper edge.
Figure 15B:
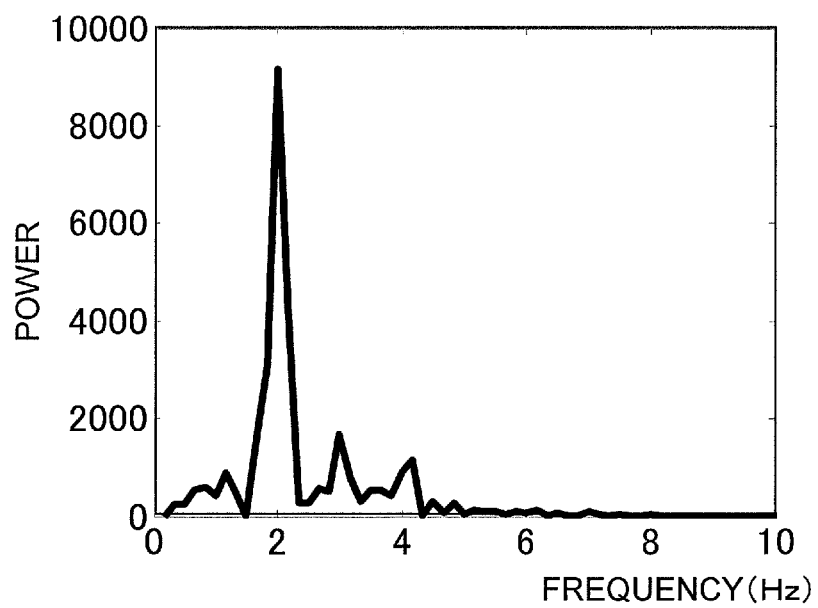
FIG. 15B is an exemplary diagram of a result of subjecting the signal of FIG. 15A to FFT for frequency analysis.

With reference to FIG. 15, characteristic features of signals associated with blinking will be described. FIG. 15A is an example of an electroencephalogram signal when blinks are made, with the ear electrode portion 11 being worn at the right mastoid and a facial electrode portion 12 being worn at the right eye-socket upper edge. Signals sharply pointed in the plus direction in FIG. 15A are electroencephalogram signals associated with blinking. In contrast to the fact that electroencephalogram signals associated with encephalic activities are normally detected with potentials within ±100 μV, signals associated with blinking have amplitudes going outside ±100 μV. FIG. 15B shows a result of subjecting the signal of FIG. 15A to FFT for frequency analysis. Electroencephalogram signals associated with blinking are generally known to appear in the δ band (0.5 Hz to 4 Hz) (see, for example, paragraph [0024] of Japanese Laid-Open Patent Publication No. 2004-350797). This particular experimental result indicates that, when signals associated with blinking are contained, strong responses will exist between 1.7 Hz and 2.2 Hz. Therefore, in the following descriptions, the frequency band from 1.7 Hz to 2.2 Hz will be defined as the frequency band for detecting electroencephalogram signals associated with blinking.

On the basis of the aforementioned characteristic features, by determining whether the measured electroencephalogram signal contains a signal in the frequency band of 1.7 Hz to 2.2 Hz and whether that signal goes outside ±100 μV or not, it can be determined whether the electroencephalogram signal contains any signal associated with blinking. For example, by subjecting the electroencephalogram signal to a 1.7 Hz to 2.2 Hz band-pass filter, only waveforms associated with blinking may be extracted, and it may be determined whether the amplitudes of those waveforms exceed ±100 μV or not.

If it is determined at step S201 that no blinking exists, detection of the position of the facial electrode portion is not performed, and the processing by the electroencephalogram measurement and determination section 13 is performed, as has been described with respect to step S105 in FIG. 13.

If step S201 finds that some blinking exists, the facial electrode position determination section 15 determines whether the electroencephalogram interface system 2 has shifted in a lower direction or an upper direction on the face. A method of determining the direction of a shift of the electroencephalogram interface system 2, i.e., a shift of the facial electrode portion 12, will be described with reference to FIG. 16.

Figure 16A:
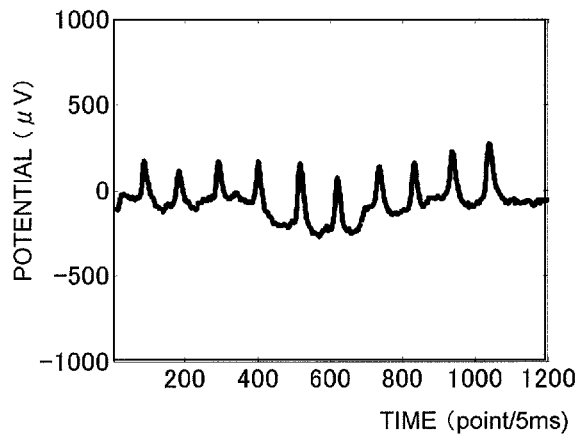
FIGS. 16A to 16C are diagrams showing exemplary electroencephalogram signals when blinks are made, with an ear electrode portion 11 being worn at the right mastoid and a facial electrode portion 12 being worn at an upper portion, a mid portion, and a lower portion of a right eye-socket upper edge, respectively.
Figure 16B:
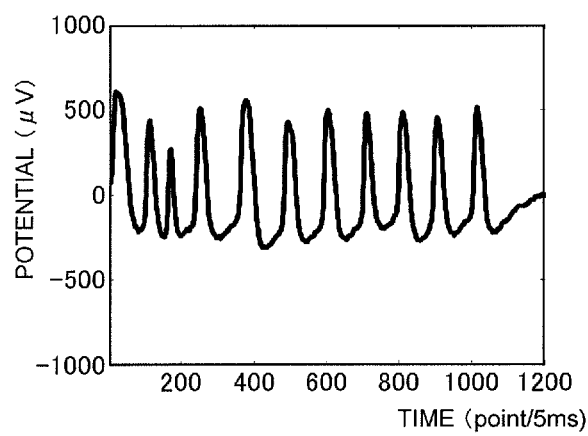
Figure 16C:
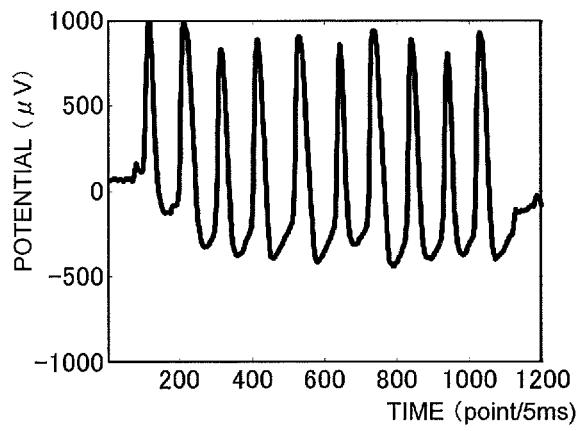

FIGS. 16A to 16C are examples of electroencephalogram signals where blinks are made, with the ear electrode portion 11 being worn at the right mastoid and a facial electrode portion 12 being worn at the right eye-socket upper edge. For the electroencephalogram signal measurement, Polymate AP-1124 (manufactured by DIGITEX LAB. CO., LTD) was used, with a sampling frequency of 200 Hz and a time constant of 1 second; as for filtering, a 30 Hz low-pass filter was used, with an active electrode being utilized. The electrode or facial electrode portion 12 was disposed at measurement positions at distances 6 cm, 4.5 cm, 3 cm from the right eye iris center, respectively being defined as an upper portion, a mid portion, and a lower portion of the eye-socket upper edge.

FIG. 16A shows an electroencephalogram signal when the facial electrode portion 12 is disposed in the upper portion of the eye-socket upper edge; FIG. 16B shows an electroencephalogram signal when the facial electrode portion 12 is disposed in the mid portion of the eye-socket upper edge; and FIG. 16C shows an electroencephalogram signal when the facial electrode portion 12 is disposed in the lower portion of the eye-socket upper edge. As shown in FIGS. 16A, 16B, and 16C, as the facial electrode portion 12 goes from above the eye-socket upper edge to below the eye-socket upper edge, signals associated with blinking increase in amplitude. This is presumably because, as has been described with reference to FIG. 22 above, the positively-charged cornea of the eyeball and the eyelid rub against each other through blinking, thus allowing the positive potential of the cornea to be transmitted to the eyelid. The reason why the noise is greater for the lower portion of the eye-socket upper edge is that the lower portion of the eye-socket upper edge is closer to the cornea, thus receiving more influence of the positive potential.

Therefore, by measuring the amplitude levels of signals associated with blinking, it becomes possible to predict which portion of the eye-socket upper edge the facial electrode portion 12 is worn at, thus enabling a determination as to whether the facial electrode portion 12 is worn at the proper position or not.

For determining a shift of the facial electrode portion 12, at step S202 of FIG. 14, the facial electrode position determination section 15 measures the amplitude of a signal associated with a blink (a signal in the frequency band of 1.7 Hz to 2.2 Hz of the measured electroencephalogram signal), and determines whether the amplitude exceeds an upper threshold value or not. Based on FIG. 16C, the upper threshold value may be set to 1200 μV, for example.

If the signal amplitude is greater than the upper threshold value, it is determined that the position of the facial electrode portion 12 has shifted below the eye-socket upper edge. Therefore, at step S203, the facial electrode position determination section 15 instructs the output section 14 to present an alarm to the user 10 for informing that "the HMD has shifted in the lower direction" or that "the HMD needs to be moved in the upper direction". By utilizing a display or a loudspeaker, the output section 14 presents an alarm to the user 10, e.g., displaying an alarm or ringing an alarm sound.

Figure 17A:
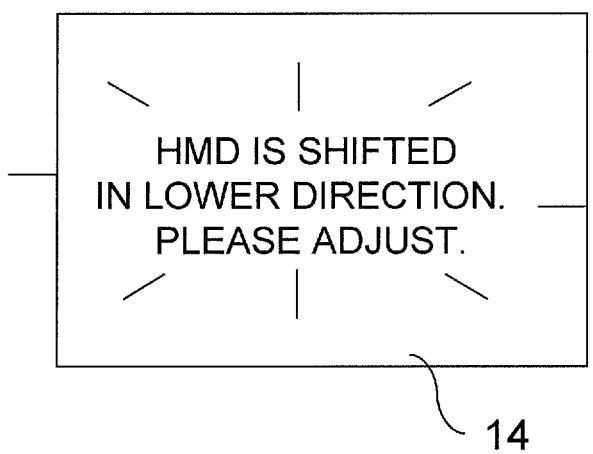
FIGS. 17A and 17B are exemplary diagrams of an alarm being presented to a user.
Figure 17B:
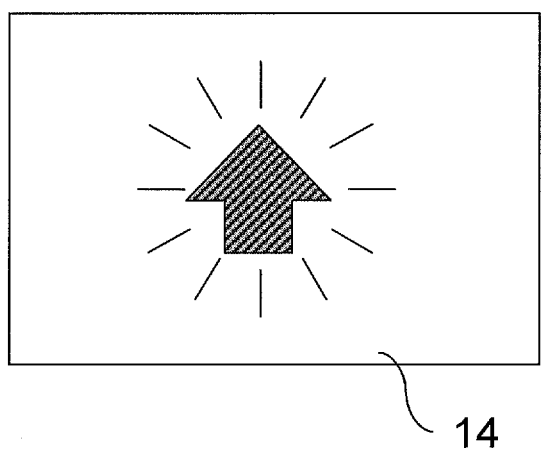

With reference to FIGS. 17A and 17B, an example of presenting an alarm to the user by utilizing the display 14 shown in FIG. 6 will be described. FIG. 17A is an example of indicating the text "HMD has shifted in lower direction. Please adjust." on the display, thus prompting the user to make an adjustment. In this case, presentation may be continued, e.g., while flickering the character sequence, until the shift of the HMD is eliminated, or displaying may be performed for a fixed time (e.g., 5 seconds) immediately after a shift occurs.

FIG. 17B is an example of presenting an alarm to the user via an icon on the display 14. If the HMD has shifted in the lower direction, the HMD needs to be moved in the upper direction, and therefore an upper arrow icon indicating the direction in which to adjust the HMD or the like is indicated on the display.

If the signal amplitude is equal to or less than the upper threshold value, at step S204 of FIG. 14, the facial electrode position determination section 15 determines whether the amplitude of the signal associated with blinking is smaller than a lower threshold value or not. Based on FIG. 16A, the lower threshold value may be set to 400 μV, for example.

If the signal amplitude is smaller than the lower threshold value, it is determined that the position of the facial electrode portion 12 has shifted above the eye-socket upper edge, and, at step S205, the facial electrode position determination section 15 instructs the output section 14 to present an alarm to the user 10 for informing that "the HMD has shifted in the upper direction". By utilizing a display or a loudspeaker, the output section 14 presents an alarm to the user 10, e.g., displaying an alarm or ringing an alarm sound. The alarm presentation method in this case is similar to the aforementioned presentation method.

If the signal amplitude is equal to or greater than the lower threshold value, it is determined that the facial electrode portion 12 is correctly worn at the eye-socket upper edge of the user 10, and alarm presentation to the user 10 is not performed.

The facial electrode position determination section continues on the determination of the position of the electroencephalogram interface system 2, along the flow of processes shown in FIG. 14 above.

As described above, based on whether the amplitudes of signals associated with blinking fall between the predetermined upper threshold value and lower threshold value, the facial electrode position determination section 15 determines the position of the facial electrode portion 12. Herein, the facial electrode position determination section 15 regards any signal in the frequency band of the 1.7 Hz to 2.2 Hz of the measured electroencephalogram signal as a signal associated with blinking. Then, if the amplitude of the signal associated with blinking do not fall between the upper threshold value and the lower threshold value, it is determined that the HMD is not correctly worn, and therefore the facial electrode position determination section 15 gives an alarm to the user 10 via the output section 14. This alarm informs the user of the presence of a shift, e.g., the fact that the HMD is shifted, or a direction in which to correct the HMD shift. This allows attention of the user 10 to be drawn to the fact that the electroencephalogram interface system 2 must be correctly worn, even in cases where the user 10 himself or herself does not notice the shift of the electroencephalogram interface system 2, e.g., (1) the position at which the electroencephalogram interface system 2 is worn is likely to shift because of the varying face shape of each individual; (2) the position at which the electroencephalogram interface system 2 is worn becomes gradually shifted in the lower direction due to the self weight of the electroencephalogram interface system 2; and (3) the position of the electroencephalogram interface system 2 has changed due to the motion, posture, and the like of the user 10. The aforementioned alarm makes it possible to measure an electroencephalogram always with the correct electrode position, thus allowing the electroencephalogram interface to operate with a stable accuracy.

Although the present embodiment adopts an approach of determining the position of the facial electrode portion 12 by utilizing blink amplitudes, the determination may be based on the amplitude levels of signals associated with eye movements, or the determination may be made through matching of the amplitude and shape of an electroencephalogram signal.

Although the present embodiment illustrates an example of presenting an alarm to the user 10 from the output section 14 when the electroencephalogram interface system 2 is improperly worn, the state of wearing the HMD may be presented to the user also when the device is properly worn. An example of such presentation is described with reference to FIGS. 18A and 18B.

Figure 18A:
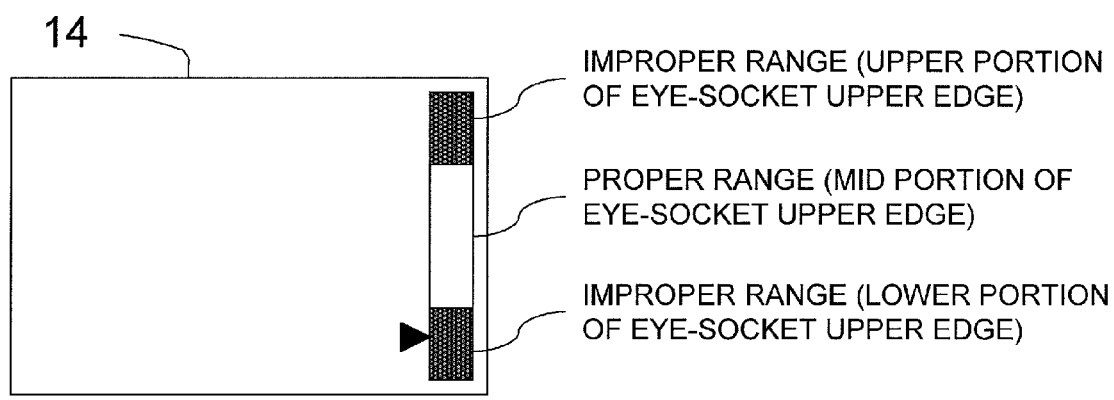
FIGS. 18A and 18B are exemplary diagrams of a notification of a state in which an HMD is worn.
Figure 18B:
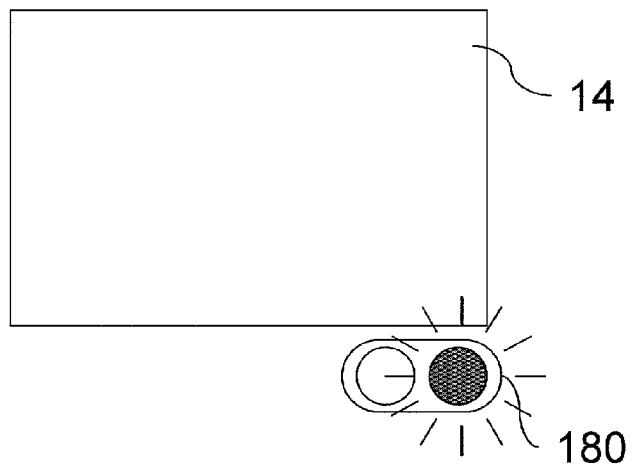

FIG. 18A shows an example where a bar indicating the range of an eye-socket upper edge is shown on the display 14 to present to the user 10 in real time the position of the facial electrode portion 12 as determined by the facial electrode position determination section 15, thus providing a notification of the state in which the HMD is worn. FIG. 18B is an example where, by utilizing LEDs 180 provided in the device or the display 14 of FIG. 6, a state in which the HMD is worn is displayed by the output section 14 in icon colors, e.g., "blue" to indicate a state of correct wearing and "red" to indicate a state of shift.

Embodiments of the present invention have been described above.

In the drawings related to the Embodiments described above, the electrodes are illustrated as circular-shaped disk electrodes which are commonly used in electroencephalogram measurement. However, this is only an example, and electrodes of any other shape may be adopted.

Figure 19A:
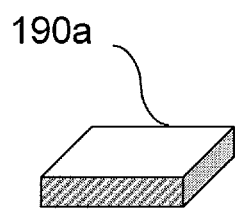
FIGS. 19A to 19C are diagrams showing electrodes of various shapes.
Figure 19B:
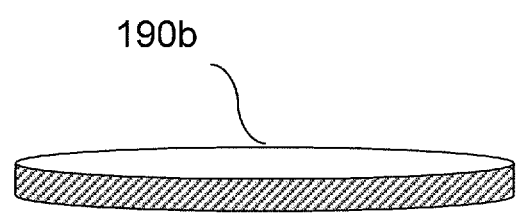
Figure 19C:
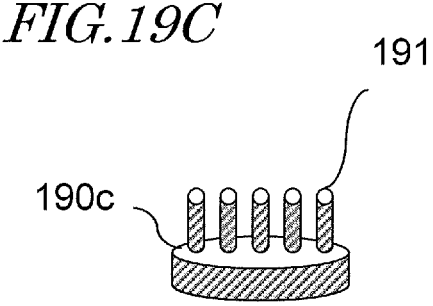

FIG. 19 shows electrodes of various shapes. FIG. 19A shows a rectangular electrode; FIG. 19B shows an elongated electrode (e.g., an ellipse or a rectangle); and FIG. 19C shows an electrode having protrusions 191 on its surface.

In the drawings related to the Embodiments above, the endpiece portions 21 are illustrated as having a shape identical to the endpiece portions of generic eyeglasses. Any other shape may be adopted for the endpiece portions 21 as well.

Figure 20A:
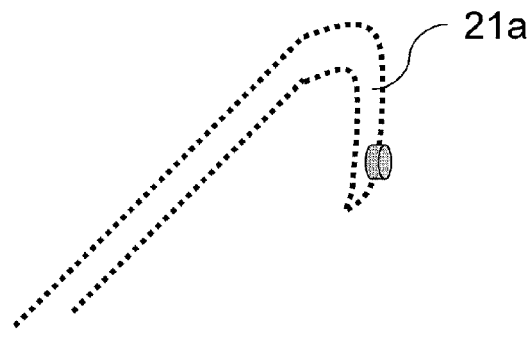
FIGS. 20A to 20D are diagrams showing endpiece portions of various shapes.

FIG. 20A shows an endpiece portion 21*a* which is shaped by curving the tip end of the earlier-described temple portion.

Figure 20B:
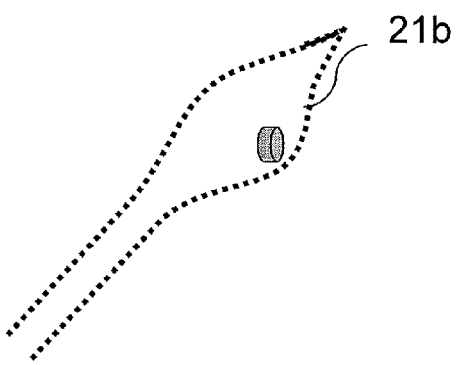
Figure 20C:
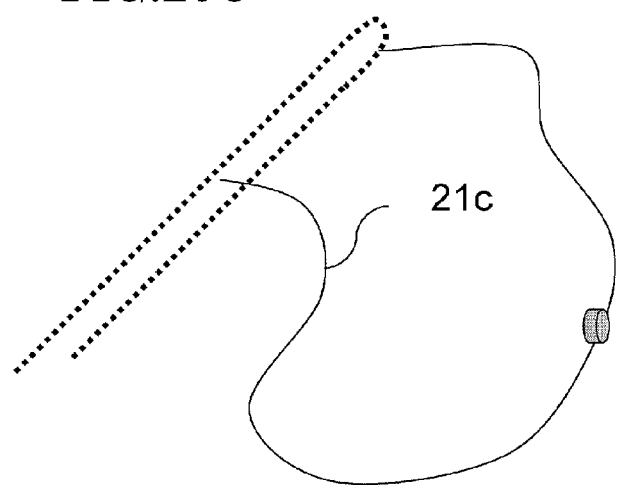
Figure 20D:
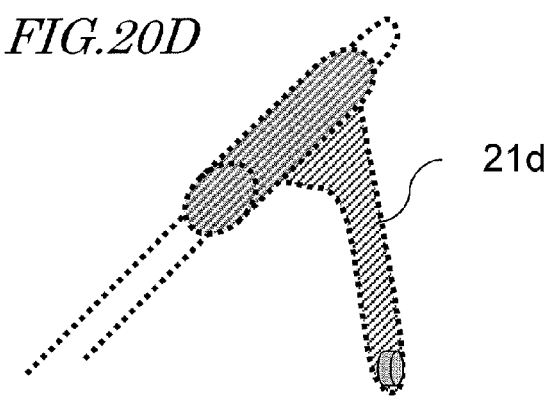

FIG. 20B shows an endpiece portion 21*b* such that the temple portion is bulged in a shape which is caught by an upper portion of an ear of the user 10. FIG. 20C shows a cord, instead of an endpiece portion, being disposed on the temple portion or the rim portion. This cord (or rubber piece) fixes the electroencephalogram interface system 1 onto an ear of the user 10. FIG. 20D shows an endpiece portion 21*d* which is inserted into the temple portion in a detachable manner. These electrode shapes indicate a possibility that, not only that the ear electrode portion 11 may be disposed in a portion of an endpiece portion, but also the ear electrode portion 11 itself may define the shape of an endpiece portion.

Furthermore, specific constructions of the elastic portion 111 (e.g. FIG. 11) described in Embodiment 2 are variously possible.

Figure 21A:
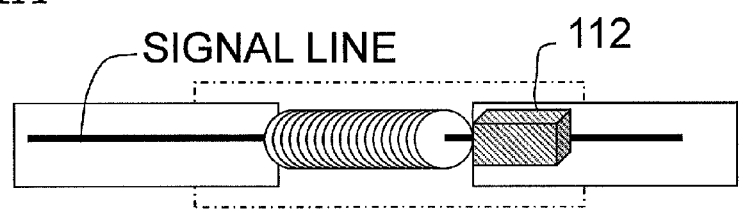
FIGS. 21A to 21C are diagrams each showing a portion of a temple portion including an elastic portion 111 and a tension detection section 112.
Figure 21B:
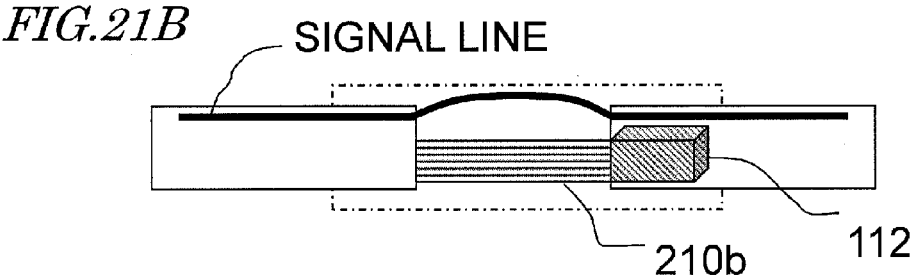
Figure 21C:
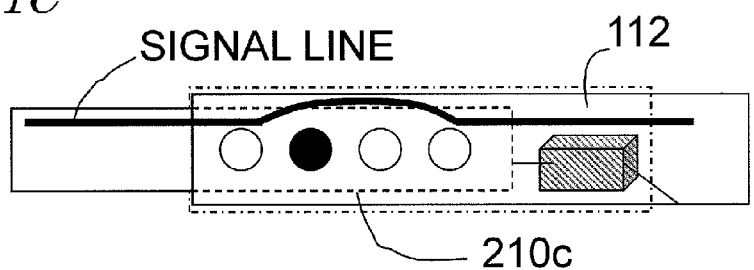

FIGS. 21A to 21C each illustrate a portion of a temple portion which includes the elastic portion 111 and the tension detection section 112.

FIG. 21A shows an elastic portion 210*a* including a spring, which was mentioned in connection with Embodiment 2. Each of rectangular parts drawn in a thin solid line indicates the temple portion, which is herein called as "temple subportion". A rectangular part drawn in a broken line indicates the elastic portion 210*a*. An elastic body such as a spring is included in the elastic portion 111, such that one end of the elastic body is connected to the tension detection section 112 and the other end is connected to a temple subportion on the endpiece portion side. When the elastic body is stretched, force is applied at the position of the elastic body connected to the tension detection section 112, thus enabling the tension detection section 112 to detect a tension, whereby the timing when the user 10 wears the HMD can be detected. A signal line for transmitting an electroencephalogram signal from the ear electrode portion 11 is connected to the facial electrode position determination section 15 and the electroencephalogram measurement and determination section 13 through the interior or exterior of the elastic body.

FIG. 21B shows an example where the elastic body is a piece of rubber rather than a spring. Thus, the elastic body may be any of various elastic bodies that are capable of undergoing changes in length, without being limited to a spring, rubber, or the like.

FIG. 21C shows an example where, rather than an elastic body, a slidable fixture 210*c* is included in the elastic portion 111. This mechanism allows the length of the temple portion to be adjusted in a stepwise manner, where a protrusion on one temple subportion fits into a hole in the other temple subportion for fixing the length. The tension detection section 112 is connected to both temple subportions, and detects a tension acting at the position of the hole which receives the protrusion of the temple portion, or a tension acting on both temple subportions, whereby the timing when the user 10 wears the HMD is detected. Note that the aforementioned method of length adjustment is only exemplary; the present invention also encompasses any mechanism that permits length adjustment in a stepless manner (e.g., via a screw), rather than in a stepwise manner.

An electroencephalogram interface system according to the present invention is broadly applicable to cases where an electroencephalogram measurement is performed on the face. Without being limited to an eyeglass-type HMD having lenses in front of both eyes, an electroencephalogram interface system according to the present invention is also available for constructing an electroencephalogram-based interface in any wearable device to be worn on the face, e.g., a wearable device to be worn on one side of the face as shown in FIG. 10.

While the present invention has been described with respect to preferred embodiments thereof, it will be apparent to those skilled in the art that the disclosed invention may be modified in numerous ways and may assume many embodiments other than those specifically described above. Accordingly, it is intended by the appended claims to cover all modifications of the invention that fall within the true spirit and scope of the invention.

What is claimed is:

1. An eyeglass-type electroencephalogram interface system having an endpiece portion, a rim portion, and a nose pad portion, and to be worn on a head of a user, comprising:
   an output section, disposed at the rim portion, and configured to present a visual stimulation to the user;
   an ear electrode portion disposed at a position coming in contact with an ear of the user when the eyeglass-type electroencephalogram interface system is worn;
   a facial electrode portion disposed at the nose pad portion coming in contact with a face of the user below a straight line connecting an external canthus and an internal canthus of an eye of the user, such that the mass of the eyeglass-type electroencephalogram interface system is supported at the nose pad portion, when the eyeglass-type electroencephalogram interface system is worn;
   an electroencephalogram measurement and determination section configured to measure an event-related potential on the basis of a potential difference between the ear electrode portion and the facial electrode portion, based on a timing of presenting the visual stimulation as a starting point; and
   a facial electrode position determination section configured to determine a position of the facial electrode portion based on whether, in the electroencephalogram signal of the user, an amplitude of a signal associated with a blink of the user falls between a predetermined upper threshold value and a predetermined lower threshold value;
   wherein the facial electrode position determination section determines that the position of the facial electrode portion has shifted in a lower direction if the amplitude of the signal is greater than the upper threshold value, and that the position of the facial electrode portion has shifted in an upper direction if the amplitude of the signal is equal to or less than the lower threshold value.

2. The electroencephalogram interface system of claim 1, wherein the ear electrode portion is disposed on a same side as the facial electrode portion with respect to the straight line connecting the external canthus and the internal canthus of an eye of the user.

3. The electroencephalogram interface system of claim 1, wherein the ear electrode portion comes in contact with the user behind an ear.

4. The electroencephalogram interface system of claim 1, wherein,
   the electroencephalogram measurement and determination section holds a determination criterion database storing data of a plurality of waveforms concerning event-related potentials;
   the determination criterion database stores data of a waveform of an event-related potential appearing when wishing to make a selection and data of a waveform of an event-related potential appearing when not wishing to make a selection; and
   the electroencephalogram measurement and determination section causes a process associated with the visual stimulation to be executed when determining that a waveform of the measured event-related potential is closest to that of the event-related potential when wishing to make a selection.

5. The electroencephalogram interface system of claim 1, wherein,
   the electroencephalogram measurement and determination section measures the electroencephalogram signal based on a potential difference between the ear electrode portion and the facial electrode portion; and
   in the measured electroencephalogram signal, the facial electrode position determination section regards a signal in a predetermined frequency band as a signal associated with a blink of the user.

6. The electroencephalogram interface system of claim 5, wherein, in the measured electroencephalogram signal, the facial electrode position determination section regards a signal in a frequency band of 1.7 Hz to 2.2 Hz as a signal associated with a blink of the user.

7. The electroencephalogram interface system of claim 6, wherein, when an amplitude of a signal associated with a blink of the user is greater than the upper threshold value or smaller than the lower threshold value, the output section presents an alarm indicating that the eyeglass-type electroencephalogram interface system is shifted in position.

8. The eyeglass-type electroencephalogram interface system of claim 1, wherein the mass of the electroencephalogram interface system acting on the nose pad portion is greater than that acting on the endpiece portion when the eyeglass-type electroencephalogram interface system is worn.

9. The eyeglass-type electroencephalogram interface system of claim 1, wherein the ear electrode portion is disposed at the endpiece portion.

* * * * *